US008192384B2

(12) United States Patent
Myrick et al.

(10) Patent No.: US 8,192,384 B2
(45) Date of Patent: Jun. 5, 2012

(54) SYSTEM FOR ENRICHING A BODILY FLUID WITH A GAS HAVING A DUAL-FUNCTION POWER SWITCH MECHANISM

(75) Inventors: Stephen E. Myrick, Tustin, CA (US); Gregory P. Watson, Laguna Niguel, CA (US); Achilles V. Young, Aliso Viejo, CA (US)

(73) Assignee: TherOx, Inc., Irvine, CA (US)

( * ) Notice: Subject to any disclaimer, the term of this patent is extended or adjusted under 35 U.S.C. 154(b) by 394 days.

(21) Appl. No.: 12/328,664

(22) Filed: Dec. 4, 2008

(65) Prior Publication Data

US 2010/0143191 A1    Jun. 10, 2010

(51) Int. Cl.
*A61M 37/00*    (2006.01)
(52) U.S. Cl. .......................................... 604/4.01; 422/45
(58) Field of Classification Search ................. 604/19, 604/45, 23, 403, 4.01–6.16; 422/45; 261/19, 261/42, 110; 48/127.9, 174; 445/23
See application file for complete search history.

(56) References Cited

U.S. PATENT DOCUMENTS

| | | | |
|---|---|---|---|
| 2,474,665 A | | 6/1949 | Guarino |
| 2,553,510 A | * | 5/1951 | Breeze .......................... 200/16 A |
| 2,770,231 A | * | 11/1956 | Falk .......................... 128/205.18 |
| 3,142,296 A | | 7/1964 | Love |
| 4,968,483 A | * | 11/1990 | Muller et al. .................... 422/45 |
| 5,213,570 A | | 5/1993 | VanDeripe |
| 5,344,393 A | | 9/1994 | Roth et al. |
| 5,865,784 A | | 2/1999 | Faithfull et al. |
| 6,582,387 B2 | | 6/2003 | Derek et al. |
| 6,613,280 B2 | | 9/2003 | Myrick et al. |
| 6,622,542 B2 | | 9/2003 | Daw et al. |
| 2005/0084416 A1 | | 4/2005 | Thomas |
| 2005/0182349 A1 | | 8/2005 | Linde et al. |
| 2007/0191990 A1 | | 8/2007 | Duan et al. |

FOREIGN PATENT DOCUMENTS

| | | |
|---|---|---|
| DE | 2343845 | 3/1974 |
| DE | 2649126 A1 | 5/1978 |
| EP | 1466637 A2 | 10/2004 |
| EP | 1372759 B1 | 8/2006 |
| EP | 1372757 B1 | 10/2006 |
| EP | 1372760 B1 | 11/2006 |
| GB | 1506555 B2 | 4/1978 |
| JP | 4095901 B2 | 6/2008 |

(Continued)

*Primary Examiner* — Tatyana Zalukaeva
*Assistant Examiner* — Benedict L Hanrahan
(74) *Attorney, Agent, or Firm* — Wei-ning Yang; Chen Yoshimura LLP

(57) ABSTRACT

This invention discloses a modular system having a base module, a mid-section control module, and a display module for preparing and administering a gas-enriched bodily fluid. An apparatus adapted for connecting with a gas tank is included in the system for gas tank hook-up. Gas-enrichment is achieved by a gas-enriching device which can be in the form of a disposable cartridge. During operation, the gas-enrichment device is placed in an enclosure within the control module. An electronic controller manages the various aspects of the system such as the production of gas-enriched fluid, flow rates, bubble detection, and automatic operation and shut down. The system has a power supply for providing electrical power to the system, and a switching mechanism coupled to the power supply and gas tank for synchronized switching of the power supply and the gas tank between an ON state and an OFF state.

4 Claims, 27 Drawing Sheets

FOREIGN PATENT DOCUMENTS

| | | |
|---|---|---|
| JP | 4156376 B2 | 9/2008 |
| JP | 4163005 A1 | 10/2008 |
| JP | 4163005 B2 | 10/2008 |
| WO | WO 92/14404 A1 | 9/1992 |
| WO | WO 92/14976 A1 | 9/1992 |
| WO | WO 95/13843 A1 | 5/1995 |
| WO | WO 96/01593 A1 | 1/1996 |
| WO | WO 96/17565 A1 | 6/1996 |
| WO | WO 96/40334 A1 | 12/1996 |
| WO | WO 96/41987 A2 | 12/1996 |
| WO | WO 97/19713 A3 | 6/1997 |
| WO | WO 97/49447 A1 | 12/1997 |
| WO | WO 98/16203 A1 | 4/1998 |
| WO | WO 98/46340 A1 | 10/1998 |
| WO | WO 99/08732 A1 | 2/1999 |
| WO | WO 99/08733 A1 | 2/1999 |
| WO | WO 02/074364 A2 | 9/2002 |
| WO | WO 02/078770 A1 | 10/2002 |
| WO | WO 02/089874 A2 | 11/2002 |

* cited by examiner (A)

(B)

Cross-section A-A

SYSTEM FOR ENRICHING A BODILY FLUID WITH A GAS HAVING A DUAL-FUNCTION POWER SWITCH MECHANISM

FIELD OF THE INVENTION

The present invention relates generally to gas-enriched fluids and, more particularly, to a system that enriches a bodily fluid with a gas.

BACKGROUND OF THE RELATED ART

This section is intended to introduce the reader to various aspects of art that may be related to various aspects of the present invention that are described and/or claimed below. This discussion is believed to be helpful in providing the reader with background information to facilitate a better understanding of the various aspects of the present invention. Accordingly, it should be understood that these statements are to be read in this light, and not as admissions of prior art.

Gas-enriched fluids are used in a wide variety of medical, commercial, and industrial applications. Depending upon the application, a particular type of fluid is enriched with a particular type of gas to produce a gas-enriched fluid having properties that are superior to the properties of either the gas or fluid alone for the given application. The techniques for delivering gas-enriched fluids also vary dramatically, again depending upon the particular type of application for which the gas-enriched fluid is to be used.

Many commercial and industrial applications exist. As one example, beverages may be purified with the addition of oxygen and carbonated with the addition of carbon dioxide. As another example, the purification of wastewater is enhanced by the addition of oxygen to facilitate aerobic biological degradation. As yet another example, in fire extinguishers, an inert gas, such as nitrogen, carbon dioxide, or argon, may be dissolved in water or another suitable fluid to produce a gas-enriched fluid that expands on impact to extinguish a fire.

While the commercial and industrial applications of gas-enriched fluids are relatively well known, gas-enriched fluids are continuing to make inroads in the healthcare industry. Oxygen therapies, for instance, are becoming more popular in many areas. A broad assortment of treatments involving oxygen, ozone, $H_2O_2$, and other active oxygen supplements has gained practitioners among virtually all medical specialties. Oxygen therapies have been utilized in the treatment of various diseases, including cancer, AIDS, and Alzheimer's. Ozone therapy, for instance, has been used to treat several million people in Europe for a variety of medical conditions including eczema, gangrene, cancer, stroke, hepatitis, herpes, and AIDS. Such ozone therapies have become popular in Europe because they tend to accelerate the oxygen metabolism and stimulate the release of oxygen in the bloodstream.

Oxygen is a crucial nutrient for human cells. It produces energy for healthy cell activity and acts directly against foreign toxins in the body. Indeed, cell damage may result from oxygen deprivation for even brief periods of time, and such cell damage can lead to organ dysfunction or failure. For example, heart attack and stroke victims experience blood flow obstructions or divergence that prevent oxygen in the blood from being delivered to the cells of vital tissues. Without oxygen, these tissues progressively deteriorate and, in severe cases, death may result from complete organ failure. However, even less severe cases can involve costly hospitalization, specialized treatments, and lengthy rehabilitation.

Blood oxygen levels may be described in terms of the concentration of oxygen that can be achieved in a saturated solution at a given partial pressure of oxygen ($pO_2$). Typically, for arterial blood, normal oxygen levels, i.e., normoxia or normoxemia, range from 90 to 110 mmHg. Hypoxemic blood, i.e., hypoxemia, is arterial blood with a $pO_2$ less than 90 mmHg. Hyperoxemic blood, i.e., hyperoxemia or hyperoxia, is arterial blood with a $pO_2$ greater than 400 mmHg, but less than 760 mmHg. Hyperbaric blood is arterial blood with a $pO_2$ greater than 760 mmHg. Venous blood, on the other hand, typically has a $pO_2$ level less than 90 mmHg. In the average adult, for example, normal venous blood oxygen levels range generally from 40 mmHg to 70 mmHg.

Blood oxygen levels also may be described in terms of hemoglobin saturation levels. For normal arterial blood, hemoglobin saturation is about 97% and varies only as $pO_2$ levels increase. For normal venous blood, hemoglobin saturation is about 75%. Indeed, hemoglobin is normally the primary oxygen carrying component in blood. However, oxygen transfer takes place from the hemoglobin, through the blood plasma, and into the body's tissues. Therefore, the plasma is capable of carrying a substantial quantity of oxygen, although it does not normally do so. Thus, techniques for increasing the oxygen levels in blood primarily enhance the oxygen levels of the plasma, not the hemoglobin.

The techniques for increasing the oxygen level in blood are not unknown. For example, naval and recreational divers are familiar with hyperbaric chamber treatments used to combat the bends, although hyperbaric medicine is relatively uncommon for most people. Since hemoglobin is relatively saturated with oxygen, hyperbaric chamber treatments attempt to oxygenate the plasma. Such hyperoxygenation is believed to invigorate the body's white blood cells, which are the cells that fight infection. Hyperbaric oxygen treatments may also be provided to patients suffering from radiation injuries. Radiation injuries usually occur in connection with treatments for cancer, where the radiation is used to kill the tumor. Unfortunately, at present, radiation treatments also injure surrounding healthy tissue as well. The body keeps itself healthy by maintaining a constant flow of oxygen between cells, but radiation treatments can interrupt this flow of oxygen. Accordingly, hyperoxygenation can stimulate the growth of new cells, thus allowing the body to heal itself.

Radiation treatments are not the only type of medical therapy that can deprive cells from oxygen. In patients who suffer from acute myocardial infarction, for example, if the myocardium is deprived of adequate levels of oxygenated blood for a prolonged period of time, irreversible damage to the heart can result. Where the infarction is manifested in a heart attack, the coronary arteries fail to provide adequate blood flow to the heart muscle. The treatment for acute myocardial infarction or myocardial ischemia often involves performing angioplasty or stenting of vessels to compress, ablate, or otherwise treat the occlusions within the vessel walls. In an angioplasty procedure, for example, a balloon is placed into the vessel and inflated for a short period of time to increase the size of the interior of the vessel. When the balloon is deflated, the interior of the vessel will, hopefully, retain most or all of this increase in size to allow increased blood flow.

However, even with the successful treatment of occluded vessels, a risk of tissue injury may still exist. During percutaneous transluminal coronary angioplasty (PTCA), the balloon inflation time is limited by the patient's tolerance to ischemia caused by the temporary blockage of blood flow through the vessel during balloon inflation. Ischemia is a condition in which the need for oxygen exceeds the supply of oxygen, and the condition may lead to cellular damage or necrosis. Reperfusion injury may also result, for example, due to slow coronary reflow or no reflow following angioplasty. Furthermore, for some patients, angioplasty procedures are not an attractive option for the treatment of vessel blockages. Such patients are typically at increased risk of ischemia for reasons such as poor left ventricular function, lesion type and location, or the amount of myocardium at risk. Treatment options for such patients typically include more invasive procedures, such as coronary bypass surgery.

To reduce the risk of tissue injury that may be associated with treatments of acute myocardial infarction and myocardial ischemia, it is usually desirable to deliver oxygenated blood or oxygen-enriched fluids to the tissues at risk. Tissue injury is minimized or prevented by the diffusion of the dissolved oxygen from the blood to the tissue. Thus, in some cases, the treatment of acute myocardial infarction and myocardial ischemia includes perfusion of oxygenated blood or oxygen-enriched fluids. The term "perfusion" is derived from the French verb "perfuse" meaning "to pour over or through." In this context, however, perfusion refers to various techniques in which at least a portion of the patient's blood is diverted into an extracorporeal circulation circuit, i.e., a circuit which provides blood circulation outside of the patient's body. Typically, the extracorporeal circuit includes an artificial organ that replaces the function of an internal organ prior to delivering the blood back to the patient. Presently, there are many artificial organs that can be placed in an extracorporeal circuit to substitute for a patient's organs. The list of artificial organs includes artificial hearts (blood pumps), artificial lungs (oxygenators), artificial kidneys (hemodialysis), and artificial livers.

During PTCA, for example, the tolerable balloon inflation time may be increased by the concurrent introduction of oxygenated blood into the patient's coronary artery. Increased blood oxygen levels also may cause the hypercontractility in the normally perfused left ventricular cardiac tissue to increase blood flow further through the treated coronary vessels. The infusion of oxygenated blood or oxygen-enriched fluids also may be continued following the completion of PTCA or other procedures, such as surgery, to accelerate the reversal of ischemia and to facilitate recovery of myocardial function.

Conventional methods for the delivery of oxygenated blood or oxygen-enriched fluids to tissues involve the use of blood oxygenators. Such procedures generally involve withdrawing blood from a patient, circulating the blood through an oxygenator to increase blood oxygen concentration, and then delivering the blood back to the patient. There are drawbacks, however, to the use of conventional oxygenators in an extracorporeal circuit. Such systems typically are costly, complex, and difficult to operate. Often, a qualified perfusionist is required to prepare and monitor the system. A perfusionist is a skilled health professional specifically trained and educated to operate as a member of a surgical team responsible for the selection, setup, and operation of an extracorporeal circulation circuit. The perfusionist is responsible for operating the machine during surgery, monitoring the altered circulatory process closely, taking appropriate corrective action when abnormal situations arise, and keeping both the surgeon and anesthesiologist fully informed. In addition to the operation of the extracorporeal circuit during surgery, perfusionists often function in supportive roles for other medical specialties to assist in the conservation of blood and blood products during surgery and to provide long-term support for patient's circulation outside of the operating room environment. Because there are currently no techniques available to operate and monitor an extracorporeal circuit automatically, the presence of a qualified perfusionist, and the cost associated therewith, is typically required.

Conventional extracorporeal circuits also exhibit other drawbacks. For example, extracorporeal circuits typically have a relatively large priming volume. The priming volume is typically the volume of blood contained within the extracorporeal circuit, i.e., the total volume of blood that is outside of the patient's body at any given time. For example, it is not uncommon for the extracorporeal circuit to hold one to two liters of blood for a typical adult patient. Such large priming volumes are undesirable for many reasons. For example, in some cases a blood transfusion may be necessary to compensate for the blood temporarily lost to the extracorporeal circuit because of its large priming volume. Also, heaters often must be used to maintain the temperature of the blood at an acceptable level as it travels through the extracorporeal circuit. Further, conventional extracorporeal circuits are relatively difficult to turn on and off. For instance, if the extracorporeal circuit is turned off, large stagnant pools of blood in the circuit might coagulate.

In addition to the drawbacks mentioned above, in extracorporeal circuits that include conventional blood oxygenators, there is a relatively high risk of inflammatory cell reaction and blood coagulation due to the relatively slow blood flow rates and large blood contact surface area of the oxygenators. For example, a blood contact surface area of about one to two square meters and velocity flows of about 3 centimeters/second are not uncommon with conventional oxygenator systems. Thus, relatively aggressive anticoagulation therapy, such as heparinization, is usually required as an adjunct to using the oxygenator.

Finally, perhaps one of the greatest disadvantages to using conventional blood oxygenation systems relates to the maximum partial pressure of oxygen ($pO_2$) that can be imparted to the blood. Conventional blood oxygenation systems can prepare oxygen-enriched enriched blood having a partial pressure of oxygen of about 500 mmHg. Thus, blood having $pO_2$ levels near or above 760 mmHg, i.e., hyperbaric blood, cannot be achieved with conventional oxygenators.

It is desirable to deliver gas-enriched fluid to a patient in a manner which prevents or minimizes bubble nucleation and formation upon infusion into the patient. The maximum concentration of solubilized gas achievable in a liquid is ordinarily governed by Henry's Law. At ambient temperature, the relatively low solubility of many gases, such as oxygen or nitrogen, within a liquid, such as water, produces a low concentration of the gas in the liquid. However, such low concentrations are typically not suitable for treating patients as discussed above. Rather, it is advantageous to use a gas concentration within a liquid that greatly exceeds its solubility at ambient temperature. Compression of a gas and liquid mixture at a high pressure can be used to achieve a high dissolved gas concentration according to Henry's Law, but disturbance of a gas-saturated or a gas-supersaturated liquid by attempts to inject it into an environment at ambient pressure from a high pressure reservoir ordinarily results in cavitation inception at or near the exit port. The rapid evolution of bubbles produced at the exit port vents much of the gas from the liquid, so that a high degree of gas-supersaturation no longer exists in the liquid at ambient pressure outside the high-pressure vessel. In addition, the presence of bubbles in the effluent generates turbulence and impedes the flow of the effluent beyond the exit port. Furthermore, the coalescence of gas bubbles in blood vessels may tend to occlude the vessels and result in a gaseous embolism that causes a decrease in local circulation, arterial hypoxia, and systemic hypoxia.

In gas-enriched fluid therapies, such as oxygen therapies involving the use of hyperoxic or hyperbaric blood, delivery techniques are utilized to prevent or minimize the formation of cavitation nuclei so that clinically significant bubbles do not form within a patient's blood vessels. However, it should be understood that any bubbles that are produced tend to be very small in size, so that a trained operator would typically have difficulty detecting bubble formation without the assistance of a bubble detection device. Unfortunately, known bubble detectors are ineffective for detecting bubbles in an extracorporeal circuit for the preparation and delivery of hyperoxemic or hyperbaric blood. This problem results from the fact that the size and velocity of some bubbles are beyond the resolution of known bubble detectors. Therefore, micro bubbles (bubbles with diameters of about 50 micrometers to about 1000 micrometers) and in some instances macro bubbles (bubbles with diameters greater than 1000 micrometers) may escape detection.

SUMMARY OF THE INVENTION

In one aspect, the present invention provides a gas-enrichment system for enriching a bodily fluid with a gas-enriched fluid, wherein the system includes an enclosure configured for receiving a gas-enrichment device; an apparatus adapted for connection with a gas tank; a controller for automatic control of system operations; a power supply for providing electrical power to the system; and a switching mechanism operatively coupled to the power supply and the gas tank for synchronized switching of the power supply and the gas tank between an ON state and an OFF state.

Other aspects and advantages of the invention will be apparent from the following description and the appended claims.

DETAILED DESCRIPTION

One or more specific embodiments of the present invention will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

System Overview

While systems of the present invention are not limited to preparation of any particular type of gas or bodily fluid, for the purpose of illustration, the following discussion will use the preparation of oxygen-supersaturated fluids and the administration of SuperSaturated Oxygen ($SSO_2$) Therapy as an example.

For the purpose of the present discussion, $SSO_2$ Therapy refers to minimally invasive procedures for enriching oxygen content of blood through catheter-facilitated infusion of oxygen-supersaturated physiological fluid. These procedures generally are aimed at treating the culprit vessel of an acute myocardial infarction (AMI) after successful percutaneous intervention (PCI) with stenting has been performed.

In a preferred embodiment, a system for administering $SSO_2$ Therapy generally includes three component devices: the main control system, the oxygen-enrichment device (i.e., the oxygenator), and the infusion device (e.g., an infusion catheter). These devices function together to create a highly oxygen-enriched saline solution called SuperSaturated Oxygen ("$SSO_2$") solution. A small amount of autologous blood is mixed with the $SSO_2$ solution producing oxygen-supersaturated blood, and then delivered to the targeted major epicardial artery via the infusion catheter. Typical duration of $SSO_2$ Therapy is about 90 minutes.

Figure 1:
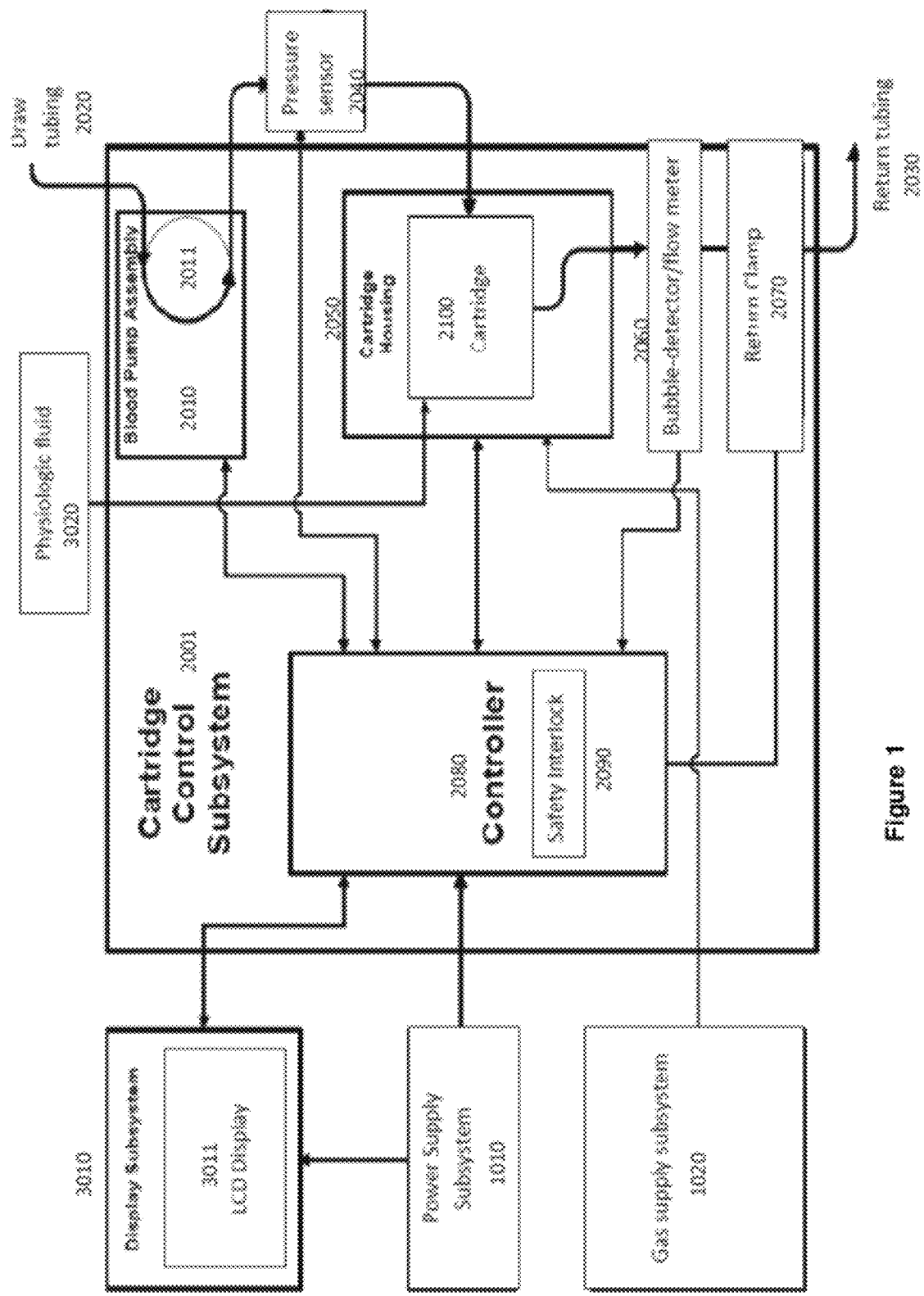
FIG. 1 shows a block diagram for an exemplary gas-enrichment system in accordance with embodiments of the present invention.

Starting with the main control system, FIG. 1 shows a block diagram that illustrates the architecture of a system in accordance with embodiments of the present invention. With reference to FIG. 1, systems in accordance with embodiments of the present invention are generally organized into a number of key subsystems, including a Display subsystem 3010 which typically comprises a display such as a LCD display 3011 for providing a user interface to the system, a Power Supply subsystem 1010 for providing power to the system, a Gas Supply subsystem 1020 for supplying the system with a gas to be used in enriching the fluid, and a Cartridge Control subsystem 2001 for automatic control of gas-enrichment and other system operations. Although a detailed discussion of the gas-enrichment device will be provided later, it is important to recognize that while in this preferred embodiment the gas-enrichment device is in the form of a cartridge, (hence the name Cartridge Control subsystem), it is not the only possible form for the gas-enrichment device. Thus, a more descriptive term for this subsystem is Gas-enrichment Control subsystem. However, for the purpose of the present discussion, the terms Cartridge Control subsystem and Gas-enrichment Control subsystem will be used interchangeably.

Functionally, the Cartridge Control subsystem is the center piece of the entire system. As shown in FIG. 1, the Cartridge Control subsystem typically comprises a controller 2080 for processing input information and issuing commands to the various components of the system. In a preferred embodiment, the controller also incorporates a safety interlock block 2090 for monitoring and ensuring the system operates within safety parameters. The safety interlock may be implemented with a logic block such as field programmable gate arrays (FPGA).

The Cartridge Control subsystem 2001 also includes a fluid pump assembly 2010 which typically comprises a pump 2011, a draw tube 2020, a pressure sensor 2040, a bubble detector/flow meter 2060, a return clamp 2070, a return tube 2030, and a Cartridge Housing 2050. The Cartridge Housing 2050 is configured to receive a matching Cartridge (i.e. the gas-enrichment device). Within the Cartridge Housing 2050 enclosure, various sensing, controlling, and interfacing mechanisms are provided for use with the Cartridge.

A physiologic fluid supply 3020 is included to provide a physiologic fluid source to the system.

Figure 2A:
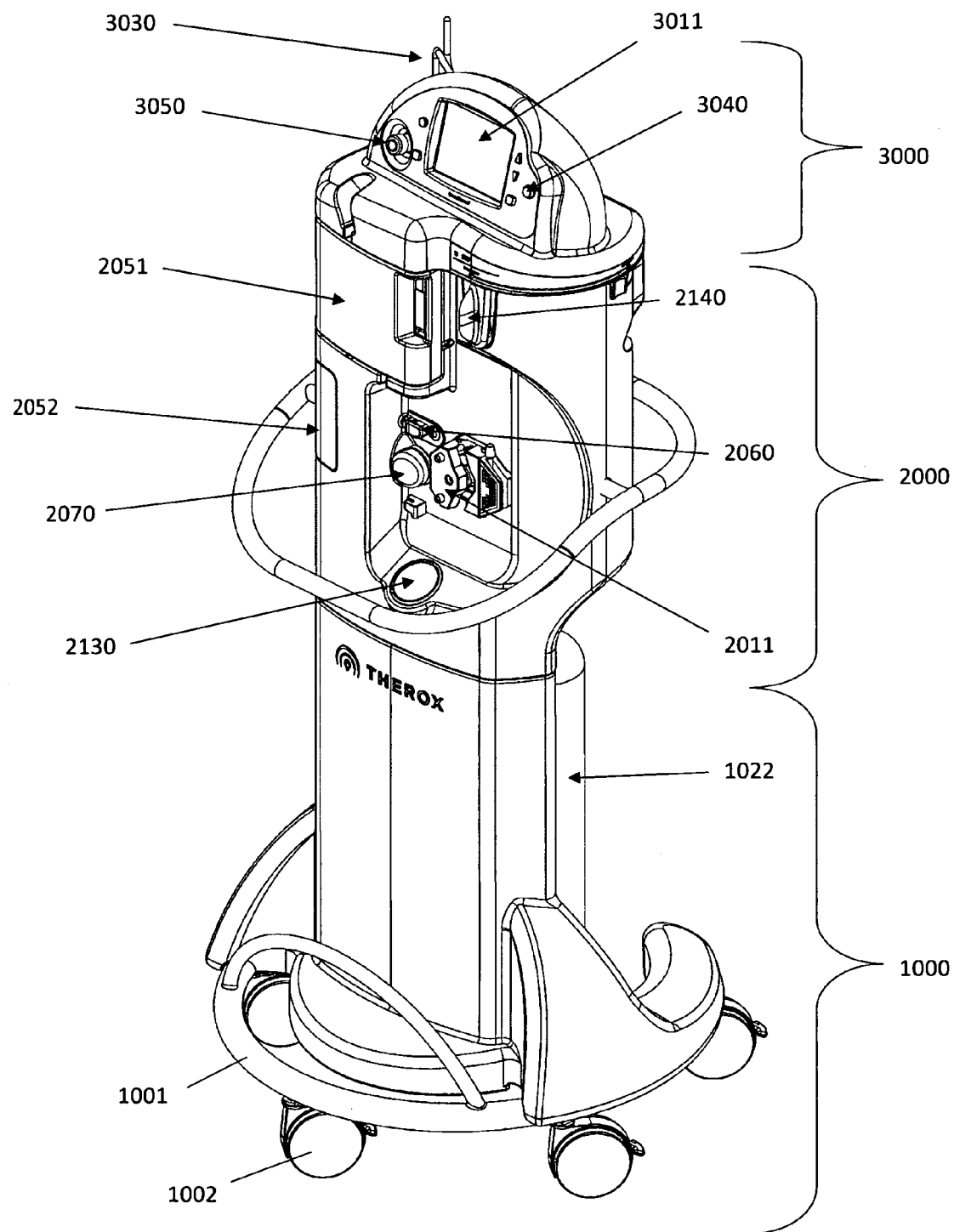
FIG. 2A shows the perspective view of an exemplary modular gas-enrichment system in accordance with embodiments of the present invention, 2B shows the base module separated from the mid-section and display modules.

It will be understood by those skilled in the art that this organizational architecture is a conceptual architecture. Actual physical implementation is a matter of design choice which may take on various physical forms. For example, FIG. 2A shows a preferred implementation of a system in accordance with the system architecture of FIG. 1. As shown in FIG. 2A, the system has a modular design comprising three removable modules, the base module 1000, the mid-section control module 2000, and the display module 3000.

Figure 2B:
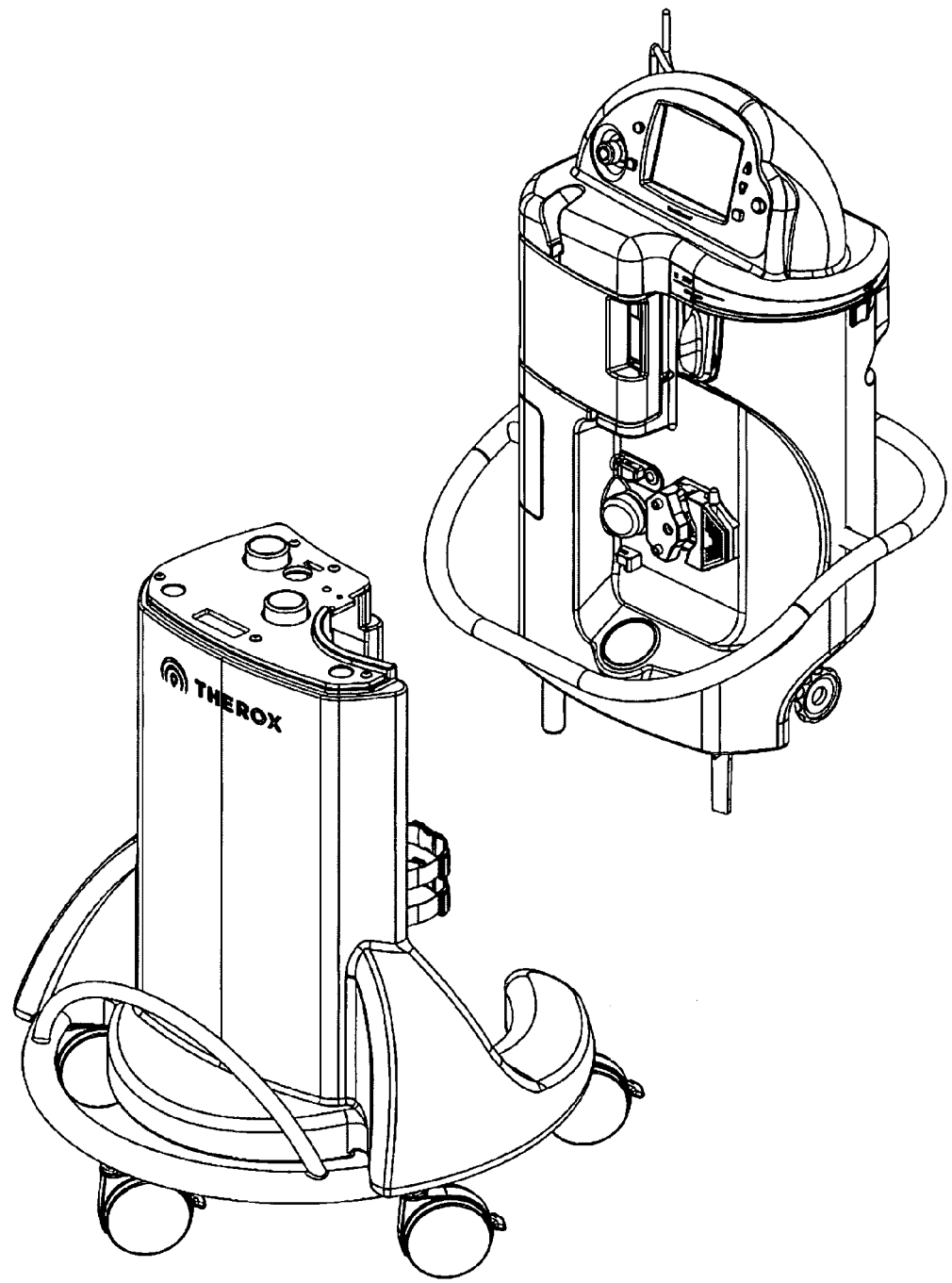

In the above particular embodiment, the body of the base module 1000 is made up of a tubular chassis situated on a circular-shaped pedestal 1001. A plurality of wheels 1002 mounted on the bottom of the circular-shaped pedestal provide mobility for the system. The wheels have a locking mechanism for keeping the wheels stationary. The base chassis houses certain electrical and mechanical components including a battery 1003 (not shown), a power supply 1004 (not shown), and connectors for connecting the base module 1000 to the mid-section main module 2000. FIG. 2B shows a configuration of the system in which the base module is separated from the mid-section and display modules.

Figure 3:
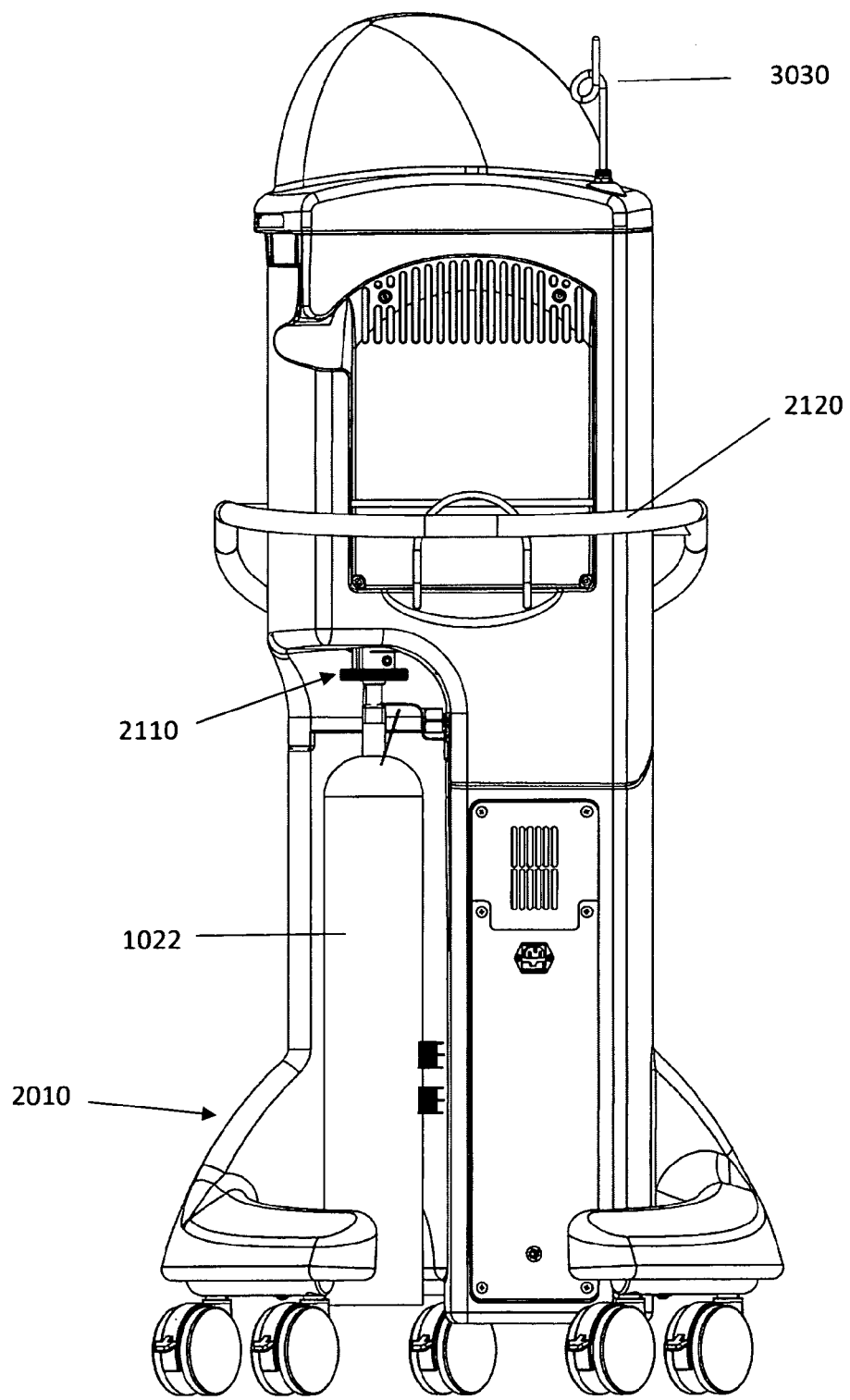
FIG. 3 shows the back view of the modular gas-enrichment system in FIG. 2.

FIG. 3 shows the back-end of the system. A gas tank receptacle 1021 is provided on the back side of the base module 1000 for receiving and housing a standard "E-bottle" USP oxygen tank 1022. The oxygen tank 1022 is mounted to the system via gas tank adapter 280.

The system is preferably sized to be convenient for use in a normal cath lab environment. While the system may be configured as a stationary device or a fixture within a cath lab, it is often desirable for various catheter-based devices to be mobile. Accordingly, in this example, wheels are provided to satisfy this contingency.

Although some of the electrical and/or mechanical components of the system may be housed in the base module 1000, these components may be placed in alternate locations of the system as a matter of design choice. To facilitate positioning of the system, a rail handle 2120 may be coupled to the mid-section control module 2000 for directing movement of the system.

Each of the three modules may include doors or access panels for protecting and accessing the various components housed therein. For example, FIG. 2 shows the mid-section control module as having a hinged door 2051 for enclosing the gas-enrichment device (i.e. the Cartridge) and access panel 2052 for covering the access window to the internal space of the module.

Referring again to FIG. 1, an appropriate draw tube 2020, such as an introducer sheath, is used to draw a bodily fluid (e.g. blood) from a patient. The drawing action is provided by the fluid pump assembly 2010. Specifically, the fluid pump assembly includes a pump 2011, such as a peristaltic pump. As the peristaltic pump 2011 mechanically produces a driving force along the flexible draw tube, fluid within the tube 2020 is pumped in the direction towards the system. A combination bubble-detector/flow meter 2060 is typically coupled to the patient's return tube 2030. Feedback from the flow meter can be used with a fluid pump assembly 2010 to operate as an automatic extracorporeal circuit that can adjust the r.p.m. (revolutions per minute) of the peristaltic pump to maintain the desired blood flow as well as provide continuous monitoring of operating parameters to ensure safety conditions are met.

The draw tube 2020 and/or the return tube 2030 may be sub-selective catheters. The construction of the return tube 2030 may be of particular importance in light of the fact that the gas-enriched bodily fluid may be gas-saturated or gas-supersaturated over at least a portion of the length of the return tube. Therefore, the return tube 2030, in particular, is typically designed to reduce or eliminate the creation of cavitation nuclei which may cause a portion of the gas to come out of solution. For instance, the length-to-internal diameter ratio of the return tube may be selected to create a controlled pressure drop and laminar flow characteristics from the oxygenation device to the patient.

Figure 23:
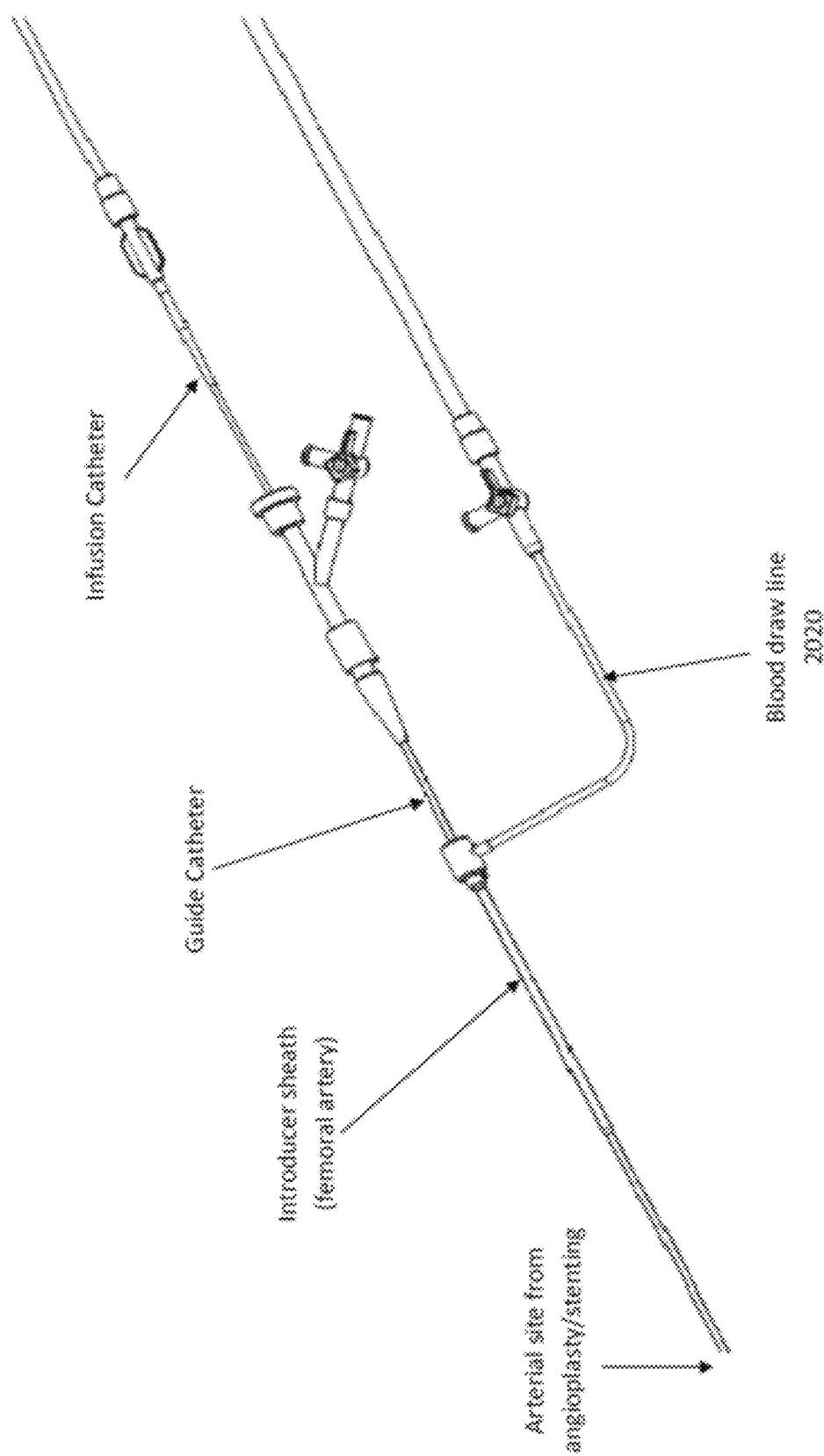
FIG. 23 shows a plane view of an exemplary extracorporeal circuit setup in accordance with embodiments of the present invention.

As shown in FIG. 23, an infusion catheter (the infusion device) is connected to the return tube for conducting the oxygen-enriched blood back to the patient. The infusion catheter is not particularly limited. Any suitable infusion catheter known in the art may be advantageously used. Typically, the infusion catheter is sized to fit within a 6 French guide catheter. Materials such as polyethylene or PEBAX (polyetheramide), for example, may be used in the construction of the catheter. Also, the lumen of the catheter should be relatively free of transitions that may cause the creation of cavitation nuclei. For example, a smooth lumen having no fused polymer transitions typically works well.

In conventional extracorporeal circuits such as those used for heart-lung machines, the tubing and oxygenation device forming the circuit must be primed with a relatively large volume of a biocompatible fluid. As fluid flows through the circuit, which are generally lengthy and may have a tortuous fluid flow path, degassing, bubble formation or bubble trapping invariably results. Thus, additional measures must be taken to eliminate air bubbles from the circuit. For example, vacuum-based gas eliminator, or membrane-based bubble filters are typically required in conventional extracorporeal lines and devices. In this regard, it is an advantage of the present invention that the fluid path formed by the draw tube and the return tube do not require large volume of fluid. More importantly, the fluid path provided has a geometry that is smooth and conducive to streamlined laminar flow, thereby reducing the risk of bubble formation due to turbulent flow conditions. As such, it should be noted that one advantageous feature of the present invention is that the fluid path may be configured to minimize bubble formation without requiring additional bubble-removing apparatus.

Exemplary geometric parameters that may affect the internal fluid flow path bubble nucleation characteristics include the cross-sectional area of the fluid stream, slope or gradient of path curvature, and surface roughness, but are not limited thereto. These parameters may be easily incorporated in the modular design of an exemplary system of the present invention to achieve an anti-bubble forming fluid flow path geometry. For example, as mentioned above, turbulence between tubing connections may have a real effect in reducing bubble formations. In general, straight-line geometries, uniform flow path diameter, and slow changing curvatures are conducive to non-turbulent flows.

Turning our attention now to the gas-enrichment device, FIG. 1 shows that the blood (bodily fluid) is to be pumped through the draw tube 2020 into the oxygenation Cartridge (gas-enrichment device) 2100. Although various different types of oxygenation devices may be suitable for oxygenating the patient's blood prior to its return, the oxygenation Cartridge of the present invention advantageously prepares an oxygen-supersaturated physiologic fluid and combines it with the blood to enrich the blood with oxygen. Also, the oxygenation Cartridge 2100 is advantageously sterile, removable, and disposable, so that after the procedure on the patient has been completed, the cartridge may be removed and replaced with another cartridge for the next patient.

The Cartridge may additionally incorporate an information recording element to record the patient's health information and procedural data so that the oxygenation cartridge is individually customized to guard against operator error. Exemplary information recording elements may include a barcode label, an RFID chip, a PROM, or any combinations thereof. Other component features and advantages of the oxygenation cartridge 2100 will be described in great detail below.

For the purposes of understanding FIGS. 1-3, it is sufficient at this point to understand that the physiologic fluid, such as saline, is delivered from a suitable supply, such as an IV bag 3020, to a first chamber within the oxygenation Cartridge under the control of a system controller 2080. A suitable gas, such as oxygen, is delivered from a gas supply, such as an oxygen tank 1022, to a second chamber within the oxygenation Cartridge. Generally speaking, the physiologic fluid from the first chamber is pumped into the second chamber and atomized to create an oxygen-supersaturated physiologic solution. This oxygen-supersaturated physiologic solution is then delivered into a third chamber of the oxygenation cartridge along with the blood from the patient. As the patient's blood mixes with the oxygen-supersaturated physiologic solution, oxygen-enriched blood is created. This oxygen-enriched blood flows from the third chamber of the oxygenation cartridge into the return tube 2030 (not shown).

When the Cartridge is loaded into the main control system, its operational status can be monitored through the display. As shown in FIG. 1, The Display subsystem 3010 provides an access point to the host/user interface of the system. The user interface is preferably implemented as a series of on-screen graphical displays such as the graphical menu system shown in FIG. 4. The pressure in the return tube are monitored by the system via, for example, a pressure sensor 2040 coupled to the return line as shown in FIG. 1.

The patient connections of the draw tube and the return tube that couple to the oxygenation device are shown in FIG. 23. In this exemplary implementation, a return pressure sensor, which is operatively coupled to the Cartridge Control subsystem, provides pressure readings to the controller 2080. The location of the pressure sensor is not particularly limited so long as the pressure being measured correspond to the desired measurement location. In some embodiments, it is envisioned that load cells may be incorporated directed in the Cartridge Control subsystem so as to eliminated the need for external pressure transducers. This configuration will have the benefit of reducing the cost necessary in embedding or coupling pressure transducers to the external lines.

The system controller may also receive a signal from a level sensor that monitors the level of fluid within the mixing chamber of the oxygenation device to ensure that the oxygen-supersaturated physiological solution is mixing with the patient's blood with little or no bubble formation.

The combination bubble-detector/flow meter 2060 represents another advantageous feature of the present system. Several convention techniques are known in the art for measuring a flow rate of a liquid flowing in a conduit, pipe, or tube. These include thermal flow meters, coriolis force flow meters, differential pressure flow meters, and ultrasonic flow meters. Generally, fluid flow meters sense one or more parameters (e.g. volumetric or mass) of the flow that can be calibrated to correspond to the rate of fluid flow. In situations where a bubble is present in the fluid, the presence of the bubble may disrupt any type of flow meter. For ultrasonic flow meters, this is particularly problematic, especially for fluids having relatively slow flow rates (e.g. <1 ml/s). Thus, in conventional applications, fluid flow measurements are usually accompanied with an independent bubble detection sensor to act as a quality control for flow rate measurements. The present invention uses a single ultrasonic probe to both detect bubbles and measure flow rate at the same time.

The combination bubble-detector/flow meter 2060 is typically positioned at the return tube 2030 to detect bubbles as they pass through the return tube to the patient. Again, as discussed in greater detail below, the system receives the signals from the ultrasonic probe and processes information regarding the nature of any bubbles that may be traveling in the oxygen-enriched blood going back to the patient. In this embodiment, the bubble detector provides this information to the host/user interface so that information regarding bubbles in the effluent may be provided to the user via the display 3011. The combination bubble-detector/flow meter 2060 may also control or shut down the system in certain circumstances as discussed in detail below.

As discussed above, the controller incorporates an interlock block 2090 that communicates with many of the components of the system for various reasons. The interlock block 2090 monitors the various components to ensure that the system is operating within certain prescribed bounds. For example, the interlock block 2090 may receive information regarding draw and return pressures from the pressure sensors, information regarding fluid level in the mixing chamber from the level sensor, and information regarding the number and/or size of bubbles from the bubble detector, as well as other information regarding the operating states of the various components. Based on this information, the interlock block can shut down the system should it begin to operate outside of the prescribed bounds. For example, the interlock block 2090 can engage the fluid pump 2011 on the draw tube 2020 and the return clamp 2070 on the return tube 2030 to stop flow of the fluid, as well as disable the blood pump assembly 2010 and the system controller 2080 that controls the oxygenation cartridge 2100.

While the interlock block 2090 typically operates in this automatic fashion, a safety switch (e.g. an emergency stop switch 3050 shown in FIG. 2) may be provided so that a user can initiate a shutdown of the system in the same fashion even if the system is operating within its prescribed bounds.

Any number of hardware implementations may be used to implement the safety interlock. In this preferred embodiment, the safety interlock 2090 is implemented using field programmable gate array chips (FPGA) and is incorporated together with the cartridge controller circuitry.

Another advantageous feature of the present inventive system is the automated priming mechanism and the small volume of priming fluid required. Relative to conventional extracorporeal circuits, the system has a far smaller priming volume requirement, typically in the range of 25 to 100 milliliters. Thus, a heater typically is not used with the system. However, if it is desirable to control the temperature of the incoming blood in the draw tube or the outgoing gas-enriched blood in the return tube, an appropriate device, such as a heat exchanger, may be operatively coupled to one or both of the tubes. Indeed, not only may the heat exchanger (not shown) be used to warm the fluid as it travels through the system, it may also be used to cool the fluid. It may be desirable to cool the fluid because moderate hypothermia, around 30° C. to 34° C. has been shown to slow ischemic injury in myocardial infarction, for example.

In this preferred embodiment, priming may be initiated by holding down the priming switch 3040. When the priming switch 3040 is released, priming action is immediately stopped. Wet-to-wet connections of various fluid tubings further reduce the priming requirement for the extracorporeal circuit and minimizes the formation of bubbles during priming.

The details of the devices and their various respective subsystems will now be described with reference to the preferred embodiment as illustrated in the remaining figures.

The Display Subsystem and the Host/User Interface

Figure 4:
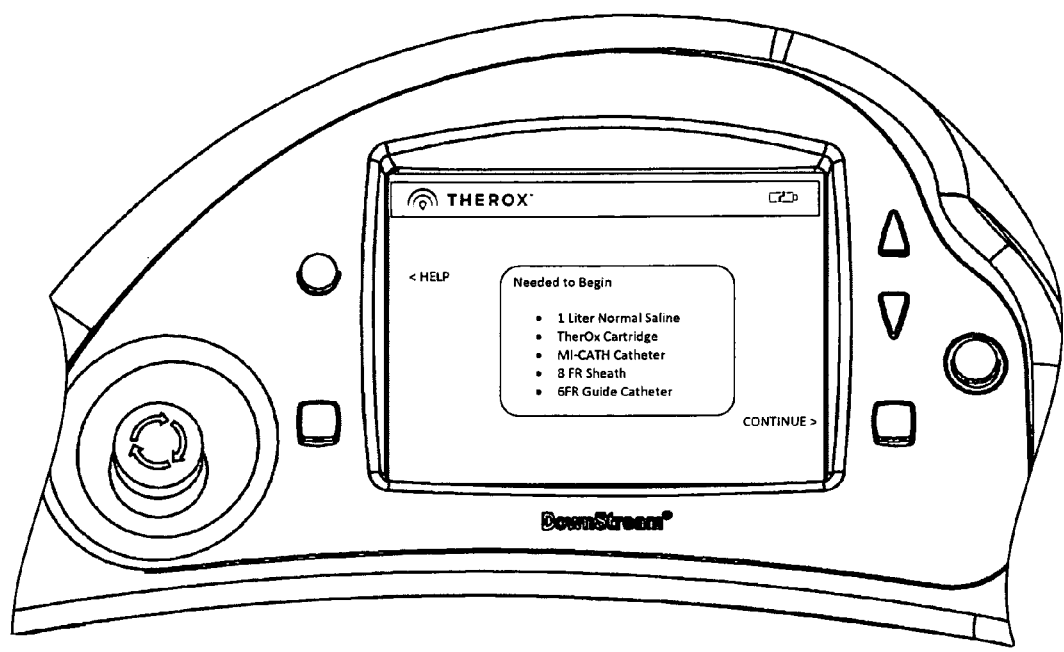
FIG. 4 shows a screenshot of an exemplary user interface display in accordance with embodiments of the present invention.

Turning now to FIG. 4, a screenshot of an exemplary embodiment of the host/user interface is illustrated. The host/user interface includes a user interface and a host interface. The user interface may include user input mechanism such as buttons, switches, and knobs. To communicate with the user, a display device, such as an LCD display, a CRT display, or a touch screen display may be used. As illustrated in FIG. 4, the display 3011 may show graphical representation of "buttons" and "pointers" to indicate to the user that a corresponding operation may be initiated by pressing the buttons as indicated. The display 3011 may also include information such as alarms/messages, status indicators, blood flow information, and bubble count. In addition, the display 3011 may also provide instructional information to the user for guiding the user in using the system.

Implementation of the Display subsystem may include a user input driver for handling user inputs and a display driver for handling actual display of the information. The user input driver transmits user inputs to an interface, such as an RS-232 interface. The RS-232 interface may communicate these user inputs to other portions of the system, such as the system controller, the interlock system, the blood pump system, or the bubble detector. The display driver communicates with a display controller, which is also coupled to the RS-232 interface via a bus. The display controller receives updated information from the various other portions of the system, and it uses this information to update the display.

The host interface may also include various other capabilities. For example, the host interface may include a sound card to drive speakers on the user interface. In addition, a network adapter may allow the host interface to communicate with an external network, such as a LAN in the hospital or a remote network for providing updates for the system, e.g., the Internet.

Figure 12:
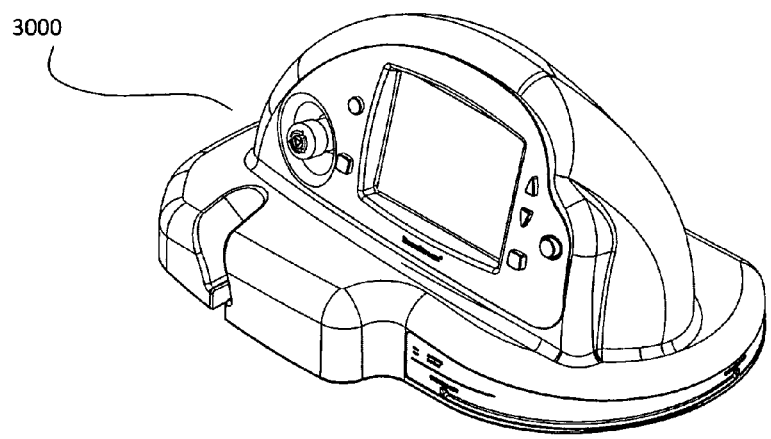
FIG. 12A shows a perspective view of the display module in the system of FIG. 2; 12B shows a key frame representation of the sequence of actions required to activate the power lever.
Figure 12:
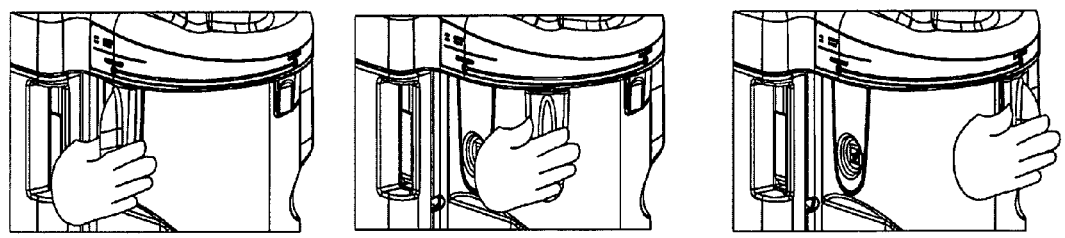

In the present preferred embodiment as shown in FIG. 2, the display subsystem is embodied in a modular casing. FIG. 12A shows a perspective view of the display module when detached from the rest of the system. The Display subsystem provides the main user interface components of the system, which preferably includes the power lever, the control buttons (including the emergency stop switch and the priming switch), and the LCD display for communicating with the user. An IV pole is also attached to provide a structure for hanging saline solution bags.

Figure 9:
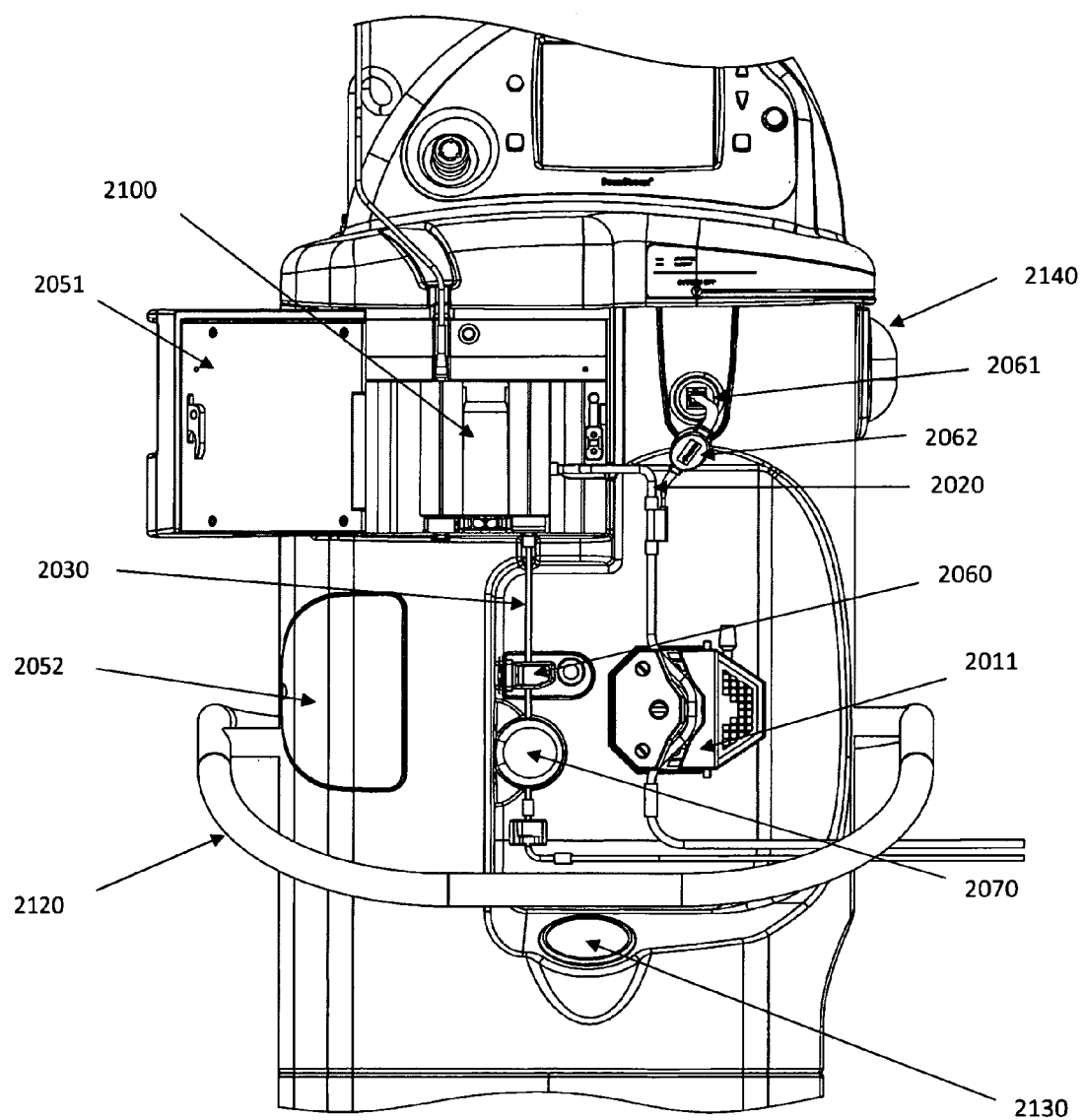
FIG. 9 shows a front view of the complete mid-section module in the system of FIG. 2.

Referring to FIG. 9, the display module is shown as already mounted on the top of the mid-section control module. In this figure, the system's power lever 2140 is located at the dividing line of the upper section and the mid-section. The power lever controls both the ON/OFF states of the entire system and also the OPEN/CLOSE states of the oxygen tank.

During operation, a user slidably moves the lever 2140 to the side of the system (the ON position) in order to turn on the system. FIG. 12B, from left to right, illustrates the sequence of actions undertaken by a user to turn the power of the system ON as well as opening the gas tank. This operation also reveals the transducer connector jack for connecting the pressure transducer to the controller. As a built-in safety feature, the system requires the user to first remove the transducer cable 2062 from the jack 2061 before returning the lever to the OFF position before the power lever can be moved to the OFF position.

As mentioned above, the power lever serves the dual role of power supply switch and oxygen tank switch. The dual function may be achieved by coupling a shaft to the oxygen valve so that sliding the lever from the OFF position to the ON position also rotates the shaft to turn on the oxygen tank.

Implementation of the user interface preferably comprises an electronic assembly including a personal computer (PC) based main circuit board (CPU), and a color liquid crystal display (LCD). The circuitry is embedded on a PCB (the display PCB). The display PCB is mounted within the modular display enclosure. The enclosure also houses the LCD. Component features of the user interface include the display PCB, the control buttons, and the LCD Display.

The display PCB preferably uses a commercially available microprocessor that provides the platform for the User Interface application software running a Linux-based operating system. This board communicates serially with the Cartridge Control subsystem.

The LCD screen displays the video output of the display PCB. A set of control buttons located around the display provide the input for user selection of application software. The display PCB provides additional functionality, analog-to-digital conversion and digital input/output capability. The user interface application software uses these functions.

The Power Supply Subsystem

The Power Supply subsystem 1010 is an electronic assembly that provides DC power to the various subsystems. The power supply 1011 receives power from the AC mains or internal batteries. Component features of the Power Supply subsystem 1010 may include: detachable power cord, appliance inlet receptacle with fuses and selection of 110-V or 220-V operation, isolation transformer, AC to DC power supply with fuse, battery with fuse, battery charger, and DC to DC power supplies, but are not limited thereto.

The isolation transformer provides electrical isolation for patient/operator protection. Batteries 1012 (not shown) are incorporated for backup power and system mobility. These batteries provide a minimum of one hour of operation when fully charged. When connected to AC Mains, the system automatically charges the batteries. The Power Supply Subsystem 1010 also includes specific DC power supplies that provide fixed voltages to other subsystems.

Preferably, the Power Supply subsystem does not require software.

The Gas-Supply Subsystem

As discussed above, the system of the present invention may be used to prepare a number of different gas-enriched fluids. In this preferred embodiment, it is an oxygen-supply subsystem 1020 that provides oxygen to the oxygenation Cartridge 2100.

FIG. 3 shows an oxygen tank 1022 loaded in the back of the system. The oxygen supply is a mechanical assembly that provides regulated oxygen to the oxygenation cartridge. The oxygen supply uses pressurized oxygen from a medical grade E-bottle, which it regulates to 750+50 psig. Component features of the Oxygen Supply include: E-bottle (yoke-type) connection, oxygen regulator with 900 psi relief valve, bottle pressure gauge, and oxygen filter. The oxygen tank is mounted to the system at the base module 1000 where an oxygen tank receptacle 2010 is provided. The oxygen tank is connected to the system via an oxygen tank adaptor 2110 located at the bottom of the mid-section control module 2000.

The oxygen supply mechanical hardware for the system is mounted on the top plate of the Cartridge Housing (to be described below). This plate contains an oxygen port that automatically connects and seals to the Cartridge's oxygen inlet upon placement of the Cartridge within the Cartridge Housing. After the oxygenation Cartridge 2100 is inserted, the closed door 2051 of the Cartridge Housing 2050 contacts an actuator that pushes the port into contact with the top of the cartridge 2100. When the door is opened, a spring retracts the port. This plate also contains tubing for conducting gas flow to the cartridge regulated by a flow valve mounted on the outside of the enclosure.

During operation, the regulator of the oxygen tank stays open to provide a constant source of oxygen gas. Flow of the oxygen gas is regulated by the oxygen flow valve which is a normally closed solenoid that is actuated by the Cartridge Controller.

A bottle pressure gauge 2130 is provided on the front panel of the system (see FIG. 2) to indicate the pressure of the oxygen tank. A relief valve is also provided to protect the system in the event that excess pressure builds up in the system. A pressure transducer located within the oxygen supply (upstream from the oxygen port) monitors oxygen pressure in the Cartridge. The transducer provides an analog pressure signal to the Cartridge Controller; this signal is measured and monitored to ensure that the pressure is within the operational limits.

The oxygen supply preferably has a standard yoke-type CGA-840 fitting, which connects to the hospital-provided oxygen bottle (E-bottle). One full E-bottle contains sufficient oxygen to support more than 50 $SSO_2$ Therapy procedures. In this preferred embodiment, the yoke is connected to a brass pressure regulator manufactured by Tescom Corporation (Elk River, Minn.).

A pressure gauge on the side of the regulator inlet measures the oxygen bottle pressure; the bottle pressure must be greater than or equal to 800 psig in order to initiate $SSO_2$ therapy. The regulator is protected from particulate debris by an inlet filter. The single-stage pressure regulator is pre-set at 750+50 psig (no user adjustment is necessary). The regulator is locked so that adjustments cannot be made to the pressure setting without a tool. A relief valve set to 900 psig is mounted on the regulator to protect the outlet side from regulator failure. The hose connects to a bulkhead fitting where the oxygen supply enters the system main enclosure. An in-line filter inside of the main enclosure protects components downstream of field service connections (bulkhead fitting). The oxygen supply connects to the oxygen valve on the cartridge control subsystem with a 1/16" tube. Approximately 2.5 L of oxygen gas (at standard temperature and pressure, STP) is necessary to pressurize the cartridge, and less than 3 ml (STP)/min is needed during $SSO_2$ Therapy administration.

Preferably, the oxygen supply subsystem does not require software.

The Cartridge Control Subsystem

Components of the Cartridge Control subsystem 2001 are mainly located in the mid-section of the system. As shown in FIG. 1, components of this subsystem may include the controller 2080, the Cartridge Housing 2050, the Cartridge 2100 (when loaded), the blood pump assembly 2011, the bubble detector/flow probe 2060, the pressure transducers 2040, and the return safety clamp 2070.

Figure 6:
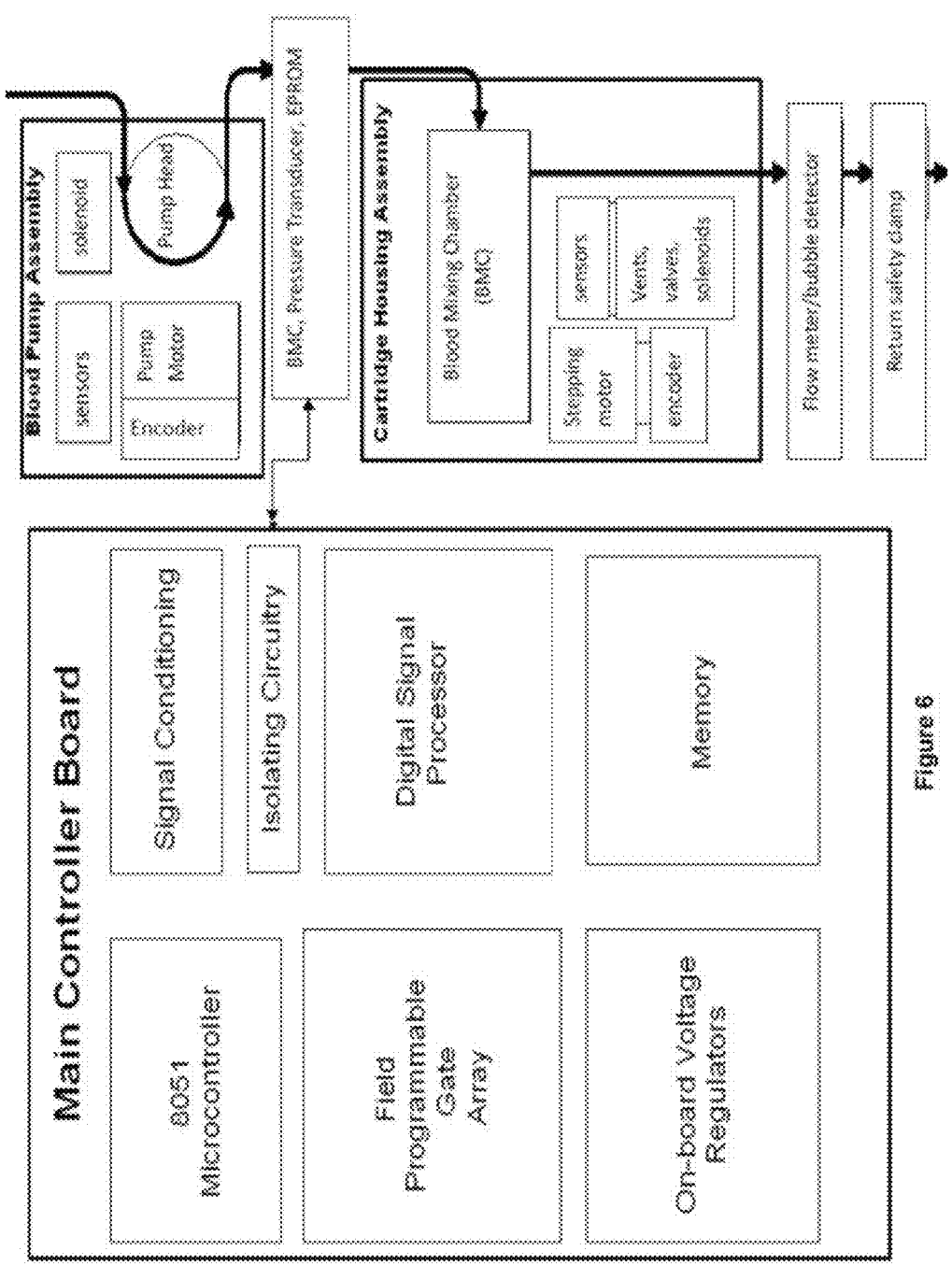
FIG. 6 shows a block diagram of an exemplary system controller in accordance with embodiments of the present invention.

The controller is the electronic assembly that monitors and controls the operation of the Cartridge during $SSO_2$ Therapy. It is made-up of a microprocessor which executes control software. FIG. 6 shows a block diagram of the system controller. The electronics of the controller is preferably implemented in a printed circuit board (PCB). The Cartridge control PCB (shown in FIG. 6 as the main controller board) receives digital and analog signals from electronic components within the system. The Cartridge control PCB also monitors the power supply voltage.

The Cartridge control PCB controls the piston actuator and all solenoids of the Cartridge controller mechanism. The Cartridge control PCB operates the fans that ventilate the main enclosure. The PCB preferably uses an 8051 microprocessor with software that controls the operating state of the system.

Figure 7:
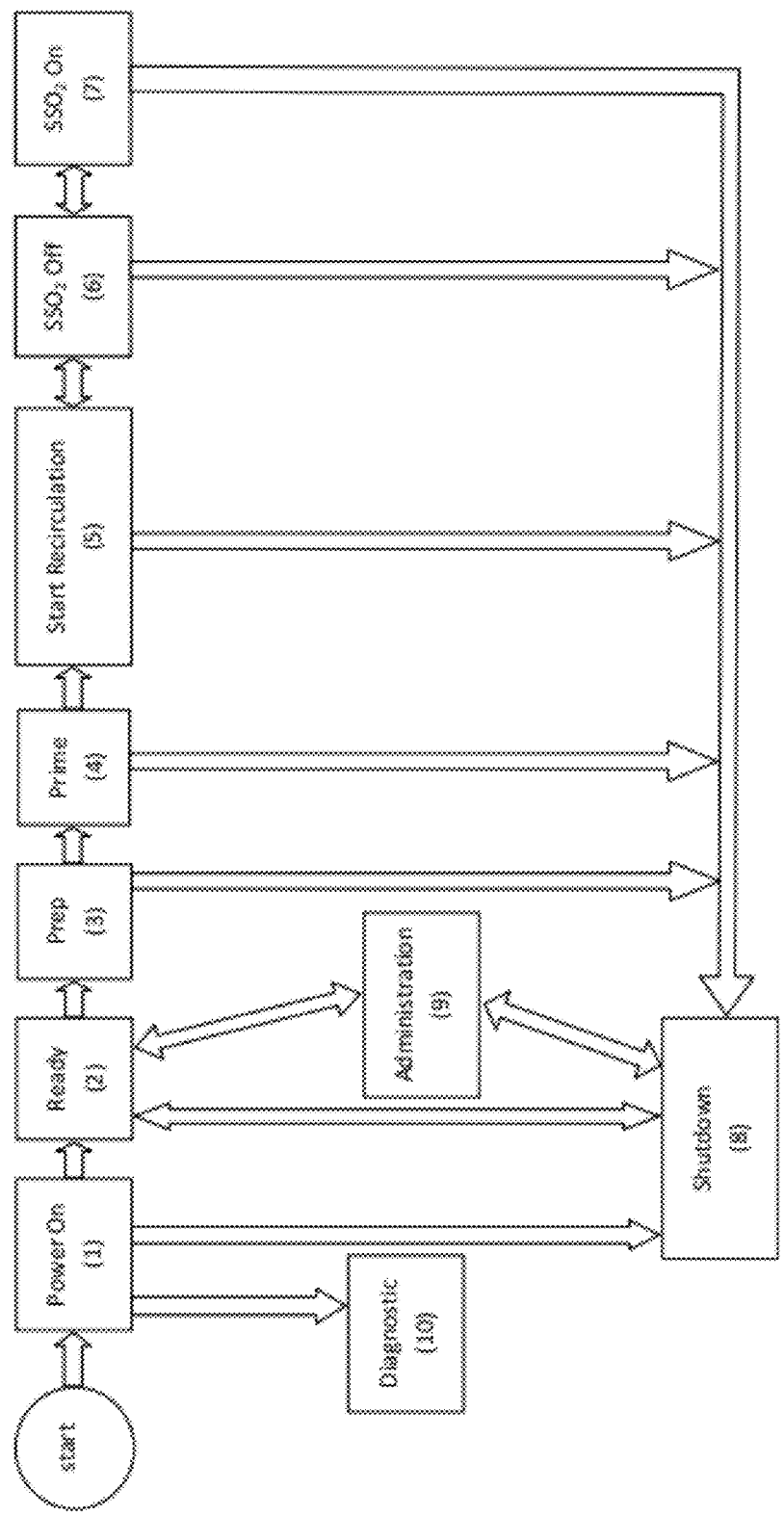
FIG. 7 shows a state diagram of an exemplary system software in accordance with embodiments of the present invention.

FIG. 7 shows a software state diagram of the control software. The software is automatically executed when the Cartridge Control subsystem is started. The control software provides ten different operating states, including: (1) Power On State; (2) Ready State; (3) Prep State; (4) Prime State; (5) Start Recirculation State; (6) $SSO_2$ Off State; (7) $SSO_2$ On State; (8) Shut Down State; (9) Administration State; and (10)

Diagnostics Mode State. The lines and arrows connecting the various different states indicate the logical relationship and transition between the connected states. This software system is preferably implemented in C++.

With reference to FIG. 7, when the system is first powered up, the software first enters the Power On state (1), during which the system runs a series of initialization tests such as testing the power supply, the internal watchdog timer, the DSP, etc. If a critical fault condition is detected during power up, the system enters the Shut Down state (8) to shutdown the system. The Power On state also offers the option to enter the Diagnostics Mode (10) which allows the user to control a specific part of the system with relaxed interlocks. Once power up is successfully executed, the system may enter into the Ready state (2).

The Ready state (2) is the state that performs Cartridge loading/unloading. If system encounters critical error during loading or unloading of the Cartridge, the system enters the Shut Down state (8). User input is then required to clear the loading/unloading error and take the system back to the Ready state (2). From either the Shut Down (8) or the Ready (2) state, user can interrupt the system to enter the Administration state (10) in order to check system parameters and perform system administrative tasks.

After the cartridge has been loaded into the Cartridge Housing, the user has spiked the saline IV bag, and the Transducer is connected to the system, the user can Prep the cartridge. The purpose of Prep state (3) is to check the Fill, Flush and Flow Valves, to saline prime the fluid path in the high-pressure side of the cartridge, establish the minimum liquid level, and pressurize with oxygen. If system encounters critical error during Prep, the system enters the Shut Down state (8). Prep is fully automated after user initiation.

Upon user input, the system may enter the Prime state (4) to prime the extracorporeal circuit. During this state, the pump is activated so long as the priming switch 3040 is pressed. Patient blood is drawn into the mixing chamber as the pump turns. Again, the Prime state (4) also offers the option of taking the system into the Shut Down state (8) when a critical fault condition is encountered or when a user input to shutdown is received. All states following the prime state will have the same option of entering the Shut Down state (8) upon encountering a critical fault condition or user input.

After the user makes wet-to-wet connection of the return tube to the infusion device, the system enters the Recirculation state (5), during which the pump continues to turn as the blood flow and return pressure stabilize. Complete circulation of fluid in the extracorporeal circuit is established during this state to finish the priming process.

When priming is completed, the system enters into the $SSO_2$ OFF state (6), during which circulation of the extracorporeal circuit is continued with no infusion of $SSO_2$ solution. Thus, the blood from the patient is only diluted slighted with the un-oxygenated saline. This state also allows the option of detecting a non-critical fault condition such as a minor occlusion in the extracorporeal tubing. When such a non-critical fault condition is encountered, the system may return to the Recirculation state (5) to re-establish proper extracorporeal circulation. If no fault condition occurs, the system will remain in the $SSO_2$ OFF state until user input is received to enter the $SSO_2$ ON state (7).

In the $SSO_2$ ON state (7), the system produces oxygenated saline, infuses the oxygenated saline with patient's blood in the mixing chamber of the Cartridge, and then return the oxygenated blood back to the patient. The system will remain in this state until completion of the therapy, user interruption, or a fault condition. Similar to the $SSO_2$ OFF state (6), the $SSO_2O$ ON state (7) also allows the option of responding to a minor non-critical fault condition by returning the system back to the previous state, thus avoiding unnecessary shutdown of the system.

This system software is preferably encoded in the controller circuitry's persistent memory (FIG. 6) so that it will be available to the system upon power up.

Also included in the controller circuitry 2080 is a safety interlock logic block for monitoring and ensuring that system operates within safety parameters. The safety interlock 2090 is basically a decision-tree logic performed by a logic device implemented with a Field Programmable Gate Array (FPGA) chip, which is integrated on the controller PCB. The FPGA circuitry is live at start-up. The safety interlock 2090 continuously monitors inputs for events that require treatment stoppage or enable treatment. The safety interlock 2090 has the ability to disable all powered electronics in the system. When certain conditions occur, the safety interlock stops treatment by disabling powered (24V) electronics, which automatically closes the return safety clamp 2070, stops the blood pump 2011, stops the piston 2161, closes the fluid flow valve, closes the oxygen valve, and depressurizes the cartridge 2100.

Exemplary function-disabling parameters monitored by the safety interlock may include signals such as: emergency stop engaged, out of range oxygen pressure transducer signal, out of range piston pressure signal, temperature high or low signal, low system voltage signal, blood pump encoder or motor failure, piston stall or encoder failure, piston top and bottom flag failure, solenoid driver open-circuit or over-temp condition, display failure or bubble detector failure, and other relevant parameters.

The safety interlock also has logic that enables functions within the Cartridge Control subsystem 2001 based on monitored inputs. For instance, the pump head 2012 will not operate if the pump head is open.

Exemplary function-enabling parameters monitored by the interlock may include: prime switch pressed, pump head open, cartridge door open, oxygen valve open, blood pump operating, cartridge detected, cartridge transducer detected, and other relevant parameters.

In addition to the above mentioned inputs to the safety interlock, a number of operating inputs may also be fed into the controller to influence system behavior, including inputs from the priming switch, and inputs from the emergency stop switch.

The priming switch is mounted to the display module. The user must press and hold to start the pump motor and initiate blood flow.

The emergency stop (E-stop) switch is also mounted to the display module. The cartridge controller disables all powered electronics (24 VDC) upon manual actuation of the E-stop switch by the system user. The E-Stop switch latches when pressed and must be manually disengaged.

It will be noted that one advantageous feature of the present invention is the automated safety responses enabled by the controller/safety interlock. In conventional extracorporeal systems, occlusion in the fluid conduits such as tubes or catheters often occurs. Vigilant monitoring by the human operator is often required to catch such occlusion events and resolve the problem by manually stopping the system, removing the occlusion, and then restarting the system regardless of the degree of the occlusion. This indiscriminate occlusion resolution procedure is both time consuming and labor intensive. Because systems of the present invention have relatively short extracorporeal path and built-in controller/safety interlock, it is possible for the system to monitor for occlusion events by monitoring changes in flow rate and/or fluid pressure, and response according to the level of occlusion. For example, if the occlusion event is minor and temporary, the controller may respond by stopping $SSO_2$ solution infusion, allowing extracorporeal circulation to restore to normal level, and notify the operator to restart $SSO_2$ solution infusion without requiring a complete shutdown of the system. In the event that the occlusion is a major and continuous, the controller may then respond by stopping $SSO_2$ solution infusion, shutting down extracorporeal circulation, and notify the operator to fix the problem before restarting the extracorporeal circulation and $SSO_2$ solution infusion.

Figure 8:
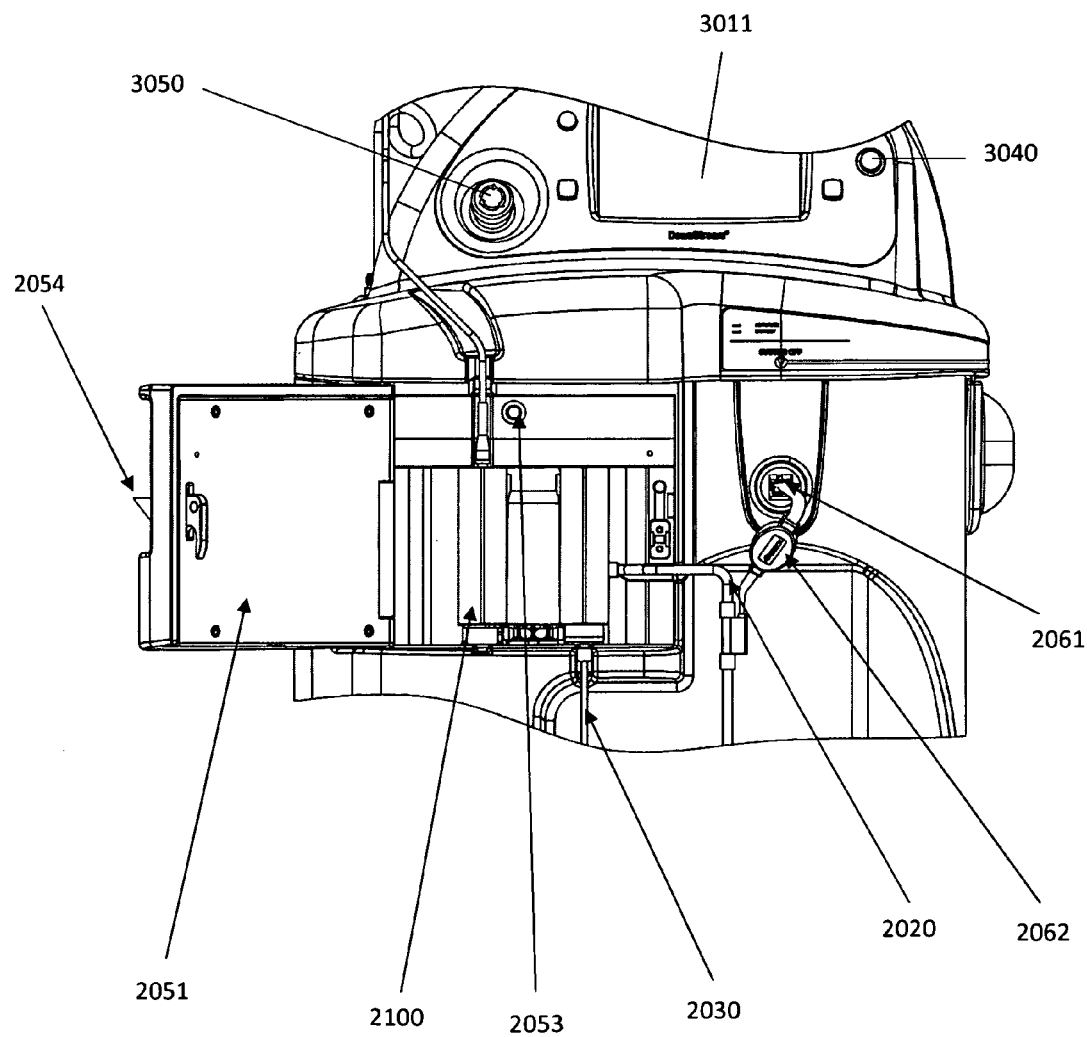
FIG. 8 shows a front view of a portion of the mid-section module in the system of FIG. 2 with a detailed view of the cartridge housing.
Figure 10:
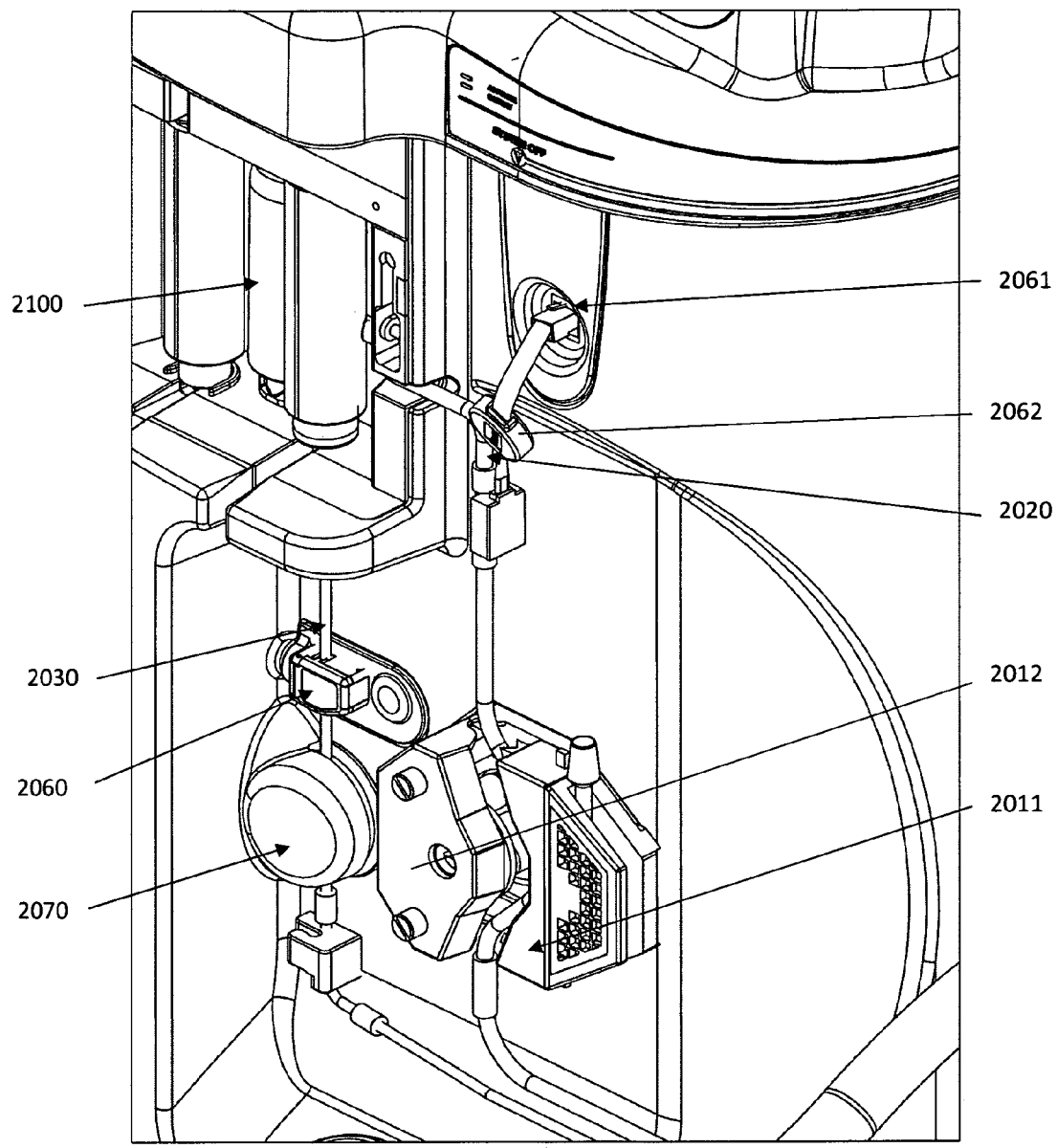
FIG. 10 shows a perspective view of the mid-section of the system in FIG. 2 with a detailed view of the fluid pump system.

Referring to FIGS. 8-10, a modular jack 2061 located on the front of the system enclosure is provided for connecting the cartridge transducer to the Cartridge Controller via a transducer cable 2062. During setup, the system user inserts the cartridge pressure transducer cable 2062 into the modular jack on the front of the system main enclosure. The analog pressure transducer input from the Cartridge is monitored by the Cartridge Controller subsystem 2001. The threshold for the blood mixing chamber pressure is set to 2000 mmHg (38 psig).

The Cartridge Housing is preferably an anodized aluminum enclosure. This housing provides a receptacle for the oxygenation Cartridge. As shown in FIG. 8, the housing assembly is embedded in the mid-section main control module 2000.

Figure 24:
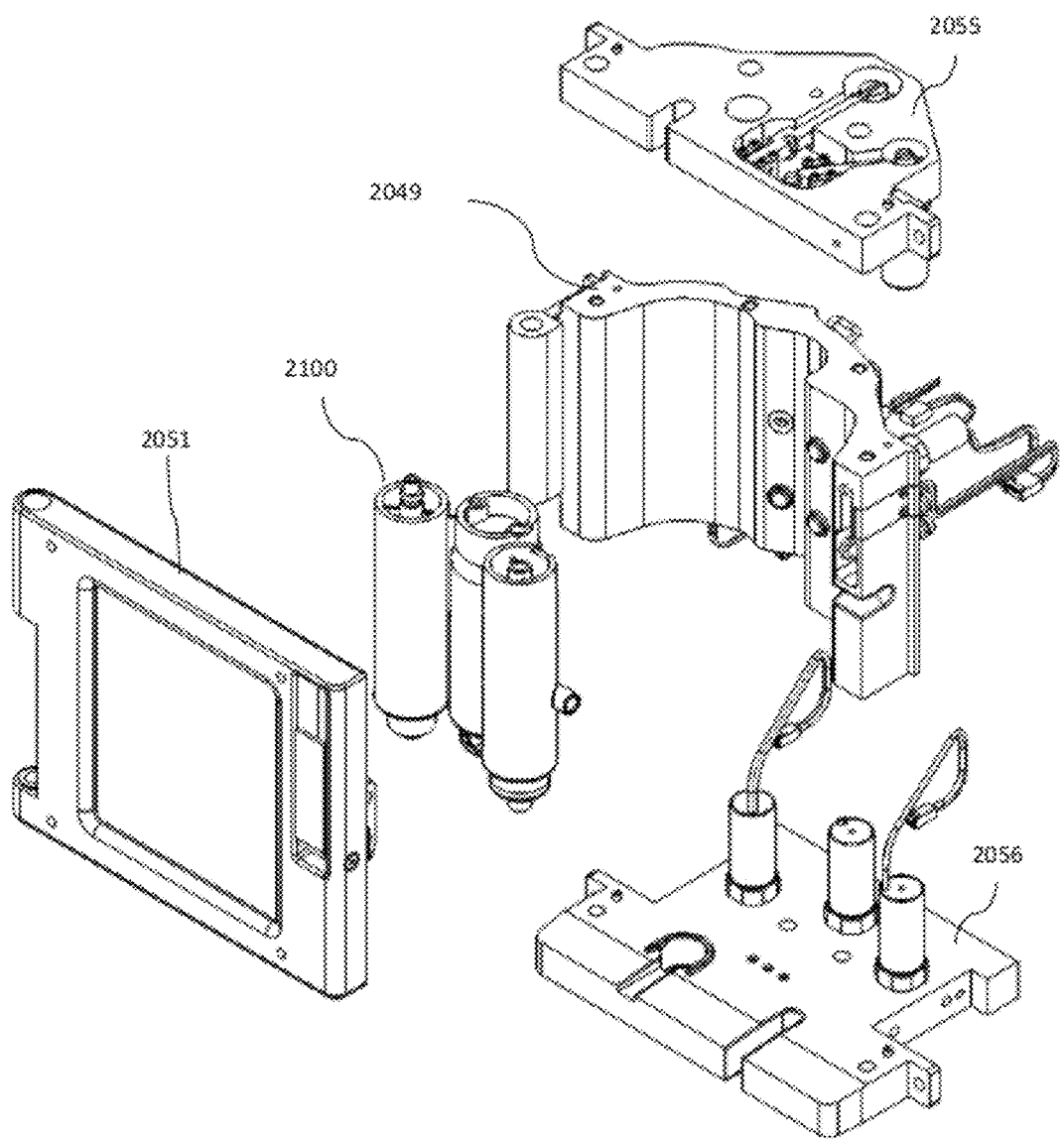
FIG. 24 shows an exploded view of an exemplary Cartridge Housing enclosure in accordance with embodiments of the present invention.

Referring to FIG. 24, the housing is formed by a receiver block 2049 for receiving the oxygenation Cartridge, a top plate 2055, a bottom plate 2056, and a door 2051.

Referring back to FIG. 8, pulling the door handle 2054 down and forward opens the door when it is unlocked. Within the housing, an LED indicator light 2053 indicates the locking state of the door. When the door is unlocked and ready to be opened, the indicator is turned on. After the door is opened, the user may insert the oxygenation Cartridge 2100 into the Cartridge Housing compartment 2050. Slots in the Cartridge Housing enable passage of the draw tubing, return tubing and IV tubing. The Cartridge 2100 is automatically aligned with all mechanical and sensor interfaces within the Cartridge Housing 2050 when the housing door 2051 is closed. The pressurized chambers of the disposable Cartridge 2100 are enclosed within the Cartridge Housing 2050. The Cartridge Housing 2050 works in conjunction with the Cartridge 2100 during operation. It has a motorized piston actuator that operates the Cartridge piston and delivers saline from an IV bag. The Cartridge Housing also has a set of needle value actuators to control the flow of liquid through the Cartridge, and vent valve actuators to depressurize the Cartridge oxygen chamber and blood mixing chamber.

The piston actuator may be comprised of a piston ram, ball screw, stepper motor, stepper motor encoder, limit switches, and load cell. The piston ram is slotted to engage a key on the cartridge piston when the cartridge is installed into the cartridge housing. The ball screw attaches stepper motor to the piston ram; it converts the rotary motion of the stepper motor into linear motion needed to operate the piston ram. The stepper motor has a rotary output that is reduced in speed and increased in torque by a gearbox. The stepper motor is driven by a stepper motor controller. The stepper motor may also include an optical encoder to detect motor speed and direction.

Two slotted IR sensors are used to detect the top and bottom position of the piston ram. A load cell measures the force applied to the Cartridge piston by the piston actuator. The load cell is a compression type donut load cell that uses strain gauge circuitry to produce analog measurements.

A solenoid-operated oxygen valve controls the flow of oxygen from the oxygen supply to the Cartridge. The valve is normally closed. The valve is pulsed open in feedback with the oxygen pressure transducer to maintain the oxygen pressure in the cartridge at the desired set point (of approximately 550 psi).

As discussed above, the Cartridge Housing has solenoid-operated actuators that control the cartridge needle valves, vent valves, and door lock actuator. Five valves within the oxygenation cartridge 2100 are controlled by three needle valve actuators and two vent valve actuators. Each valve actuator mechanism has a pin on one end of a lever and a pull-type solenoid on the other. The oxygen vent valve has a spring that pushes the pin away from the vent valve to maintain the valve open when the solenoid is not energized. For the other four valves, a spring preloads the lever, pushing the pin against the cartridge needle valve or vent valve to maintain the valve closed when the solenoid is not energized. When energized, the solenoid pulls the pin away from the needle or vent valve, allowing the valve to open from pressure inside the cartridge. The door lock has a spring that engages the lock mechanism when the solenoid is not energized.

The Fluid Pump Assembly

Referring again to FIG. 1, the Cartridge Control subsystem 2001 includes a fluid pump assembly 2010, which brings together the fluid pump 2011, the combination bubble-detector/flow meter 2060, the draw tube 2020, the return tube 2030, and the return safety clamp 2070 to modulate fluid flow through the system.

When the system is used in $SSO_2$ therapy, the fluid pump withdraws arterial blood from the patient and pumps it through the oxygenation cartridge 2100 and the infusion catheter back to the patient (see FIG. 23). The fully occlusive peristaltic blood pump 2011 interfaces with the cartridge tubing and thus does not have direct fluid contact. The system user inserts the draw side tubing 2020 into the pump head and the return side tubing 2030 into the flow probe during system set-up. FIGS. 9 and 10 show the visible components of the blood pump 2011.

The pump head 2012 is coupled to the DC motor mounted inside the enclosure of the mid-section control module. The pump head 2012 and the combination bubble detector/flow meter 2060 are mounted on the front of the module enclosure. The blood pump 2011 operates at a fixed flow rate of 75 ml/min, set by software. The blood pump supports the 75 ml/min flow rate set point at hydrodynamic pressures less than or equal to 35 psig. Component features of the blood pump include: pump head 2012, pump head detector 2013, pump motor 2014, and pump lock 2015.

The pump head 2012 is a three-roller peristaltic pump head mounted on the front of the system main enclosure. The occlusion setting is fully occlusive for the tubing, so the pump head 2012 functions as a tubing clamp when stopped. The peristaltic pump features an over-center, cam-actuated mechanism with a handle 2016 to facilitate loading of tubing. The pump head shaft is coupled to the blood pump DC motor.

The blood pump 2011 has a sensor to detect if the pump head is closed. This IR sensor detects a reflective feature when the pump head is in the closed position and provides an electrical signal to the controller 2080. The pump motor 2014 will not turn when the pump head 2012 is in the open position.

The blood pump motor 2014 assembly is a DC servomotor with optical encoder and gearbox. The motor speed is regulated by the cartridge controller PCB using Pulse Width Modulation (PWM). This circuit provides consistent pump speed operation independent of load, line voltage and temperature variations. The controller PCB uses an analog input from the blood flow measurement to maintain the flow rate set point, and sends this analog signal to the Safety Interlock. The pump motor shaft has an optical encoder with a revolution index output that is measured by the controller PCB.

The blood pump incorporates a custom locking mechanism which only opens to allow loading or unloading of draw tubes. This prevents inadvertent opening of the pump head during operation.

Figure 11:
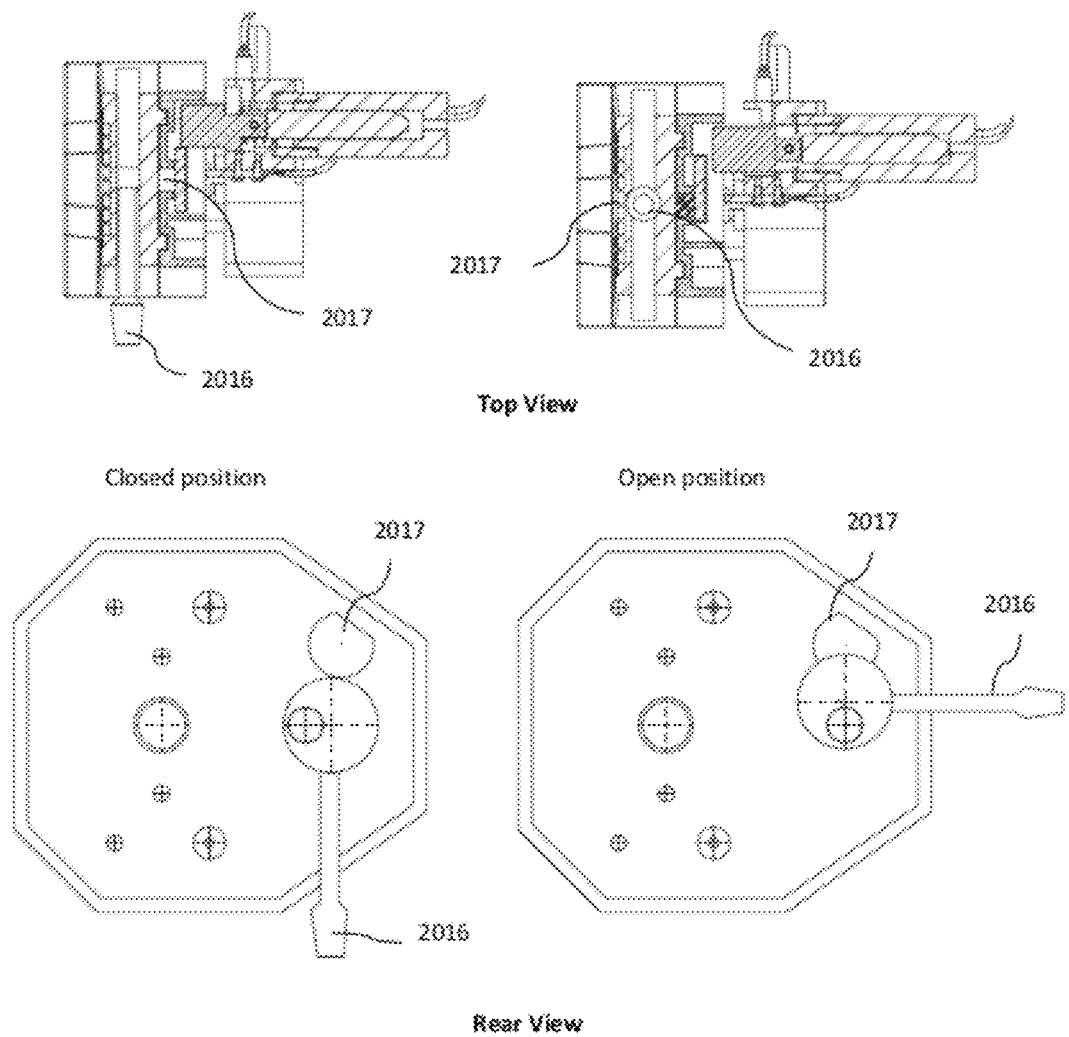
FIG. 11 shows a schematics view of the pump locking mechanism in the system of FIG. 2.

FIG. 11 illustrates an exemplary locking mechanism in accordance with the present invention. In the present preferred embodiment, the pump has a pump lever 2016 connected to an off-center cam 2018. When the lever 2016 is placed in the open position, the cam blocks the pump lock latch 2017 so the lock cannot be engaged. When the lever is placed in the closed position, the cam is rotated out of the way so that the pump lock latch 2017 can be fully engaged. Once the latch 2017 is engaged, it blocks the cam so that the lever cannot be rotated into the open position, thereby, preventing accidental opening of the pump head once the lock is engaged.

Combination Bubble-Detector/Flow Meter

The bubble detector/flow meter 2060 is a combination device which performs both the functions of bubble detection and flow measurement. As shown in FIGS. 1, 2, 9 and 10 of the present preferred embodiment, the combination bubble detector/flow meter 2060 is an ultrasonic device mounted on the mid-section control module, and is coupled to the return tube 2030. The bubble detector/flow probe 2060 communicates with a digital signal processor (DSP) on the controller PCB to continuously monitor the return blood path for air bubbles. The DSP has software that counts and calculates the size of each bubble that passes through the return tubing. The bubble detection function of the combination detector 2060 is capable of counting individual bubbles as small as 100-μm in diameter. The bubble detector DSP software also calculates a cumulative bubble volume. If the cumulative bubble volume reaches 10 μl during the 90-minute treatment, or signal strength is out of range, the Bubble Detector initiates a system shutdown. Measurement of bubble uses a time-of-flight measure which compensates for environmental variances.

In the present preferred embodiment, the ultrasonic probe has a pair of crystals oriented across the fluid path at a 45-degree angle. The signal can be sent in either direction, but one direction is upstream and the other is downstream. After data has been collected by the Data Collection State Machine, the difference in the upstream and downstream data is used to calculate the fluid flow. The flow rate is calculated on the difference between the two measured phases of the collected data.

Figure 5:
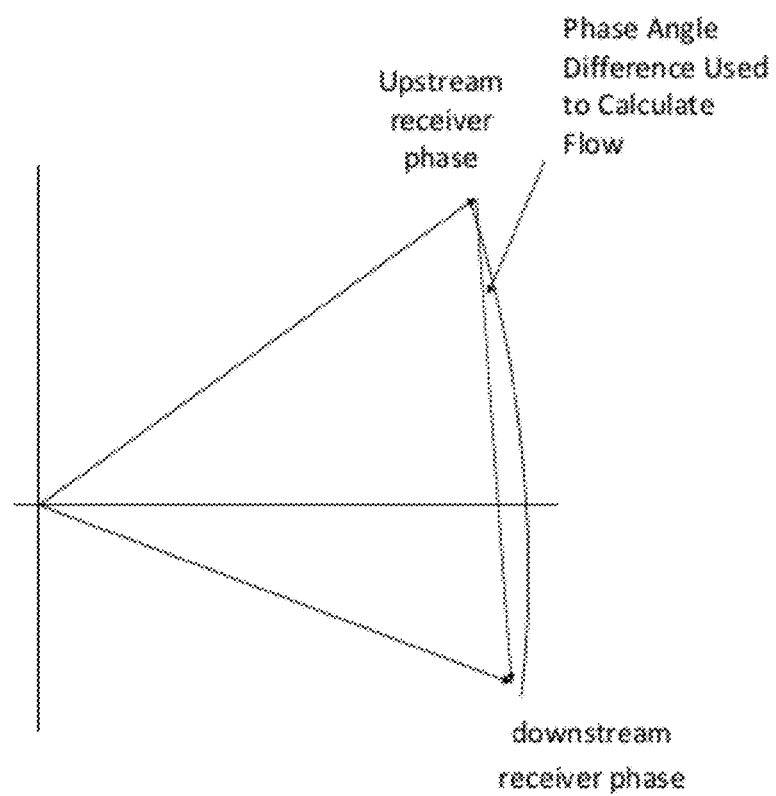
FIG. 5 shows a diagram illustrating the phase angle of the transceivers in a combination bubble detector/flow meter in accordance with embodiments of the present invention.

The flow rate is proportional to the differences between the two phase angles as depicted in FIG. 5, so time-of-flight measurements can be done by calibrating the phase angle differences against a known flow rate first and then using the proportionality to determine other flow rates. Detection range can be in the range of about 1-200 ml/min.

The bubble detector/flow probe digital signal processor (DSP) process signals received from the bubble detector/flow meter transducer according to its software. Software algorithms in the DSP measure the electrical signal attenuation that occurs when a bubble passes through the transducer. The bubble size is proportional to the magnitude of the attenuation. The DSP feeds input to the cartridge controller which has software algorithms to count bubbles and calculate the accumulated bubble volume. The bubble detector DSP provides serial communication to the cartridge controller for accumulated bubble volume, and sends/receives digital signals to/from the safety interlock.

Figure 25:
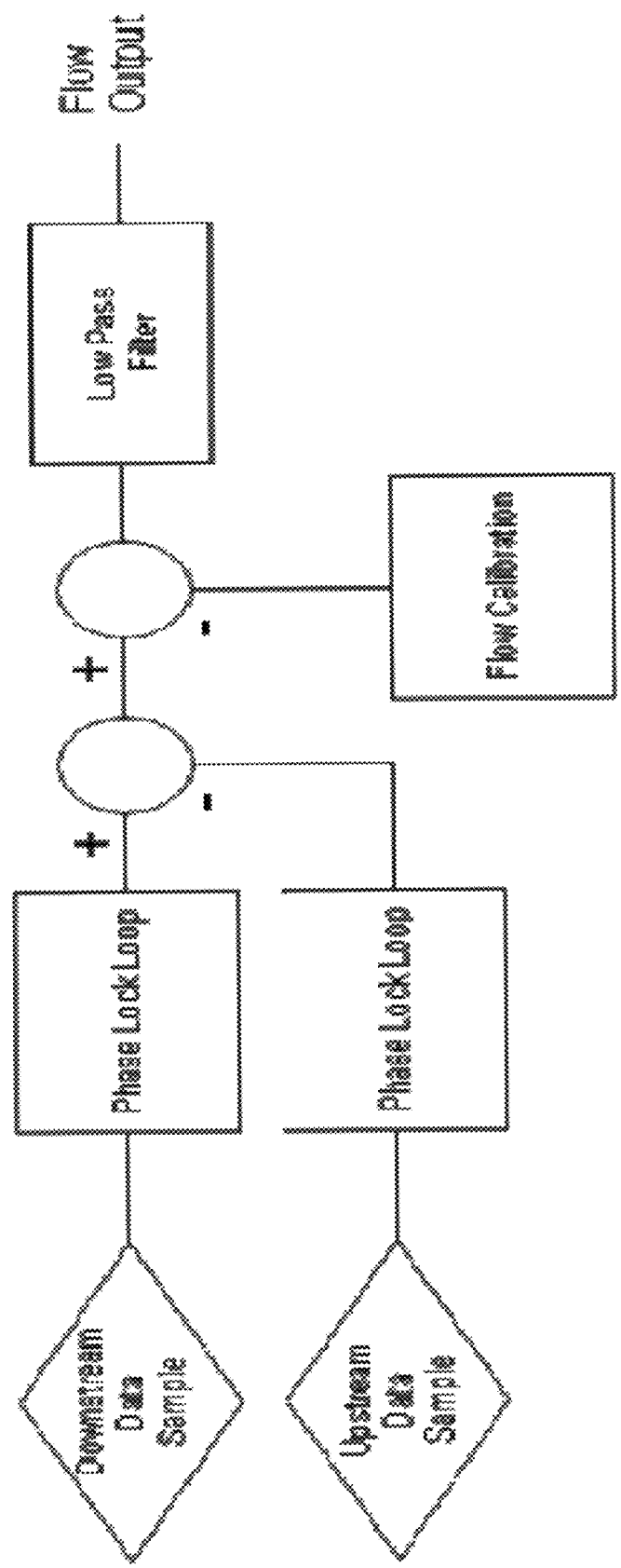
FIG. 25 shows a block diagram illustrating the algorithm for flow rate measurement in accordance with embodiments of the present invention.

FIG. 25 is a block diagram illustrating the algorithm in accordance with the present invention for flow calculation. The procedure to calculate the flow rate first calculates the upstream and downstream phases by running a phase lock loop algorithm against the sampled data. The phase lock loop calculates the in phase and quadrature phase signal amplitudes, and then forces the quadrature phase value to zero. The output of the phase lock loop is the phase angle that it takes to keep the in phase signal peaked against the input data. The difference between the phase angle is calculated, and a calibration offset is added. The calibrated flow measurement is then passed through a low pass filter for clean up.

Figure 26:
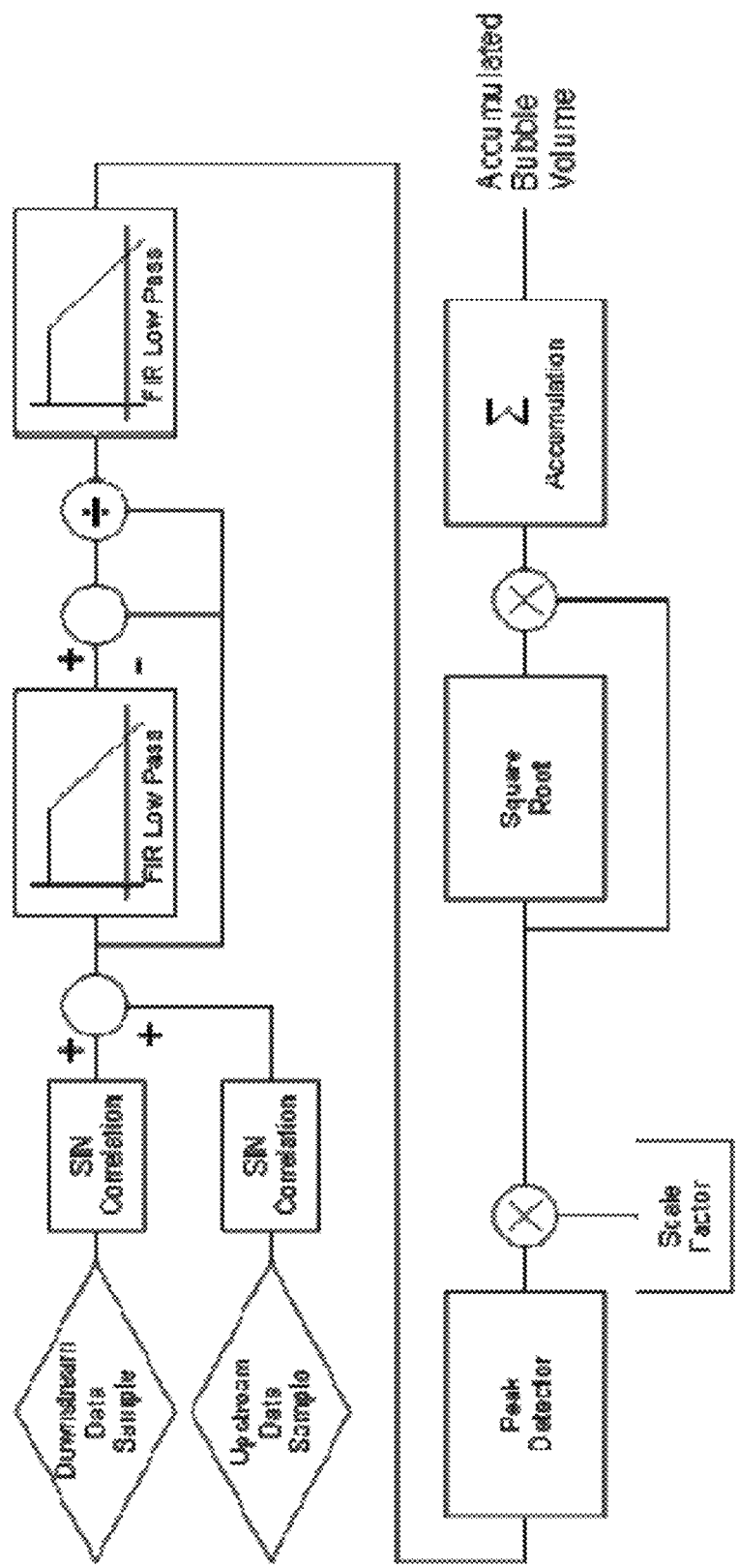
FIG. 26 shows a block diagram illustrating the algorithm for bubble detection in accordance with embodiments of the present invention.

FIG. 26 is a block diagram illustrating the algorithm in accordance with the present invention for bubble detection. The bubble detection process involves calculating the upstream and downstream signal amplitudes and averaging them, checking the signal level against a lower limit threshold, peak detecting the signal, and determining the end of bubble state.

The peak detector is first checked for signal above the noise threshold. Once a signal has been detected, the sample by sample peak is calculated. A peak is qualified when either the signal drops below the noise threshold, or reaches a relative minimum and then rises above the relative minimum plus the noise threshold. The peak detection scheme is designed to respond to bubbles that are closely spaced, or even overlapping in the sensor.

Once a bubble peak has been captured the resulting peak is first scaled to reflect a normalized area, because the measured ultrasonic signal attenuation is proportional to the projected 2-D area of the bubble. The area is then divided by PI ($\pi$) and the square root is taken resulting in the radius. The radius is then multiplied by the scaled area and then by 4/3 to generate the bubble volume. Individual bubble volumes are added to generate the accumulated bubble volume. The accumulated bubble volume is then passed up to the host system for further processing.

Referring again to FIG. 2A, a return safety clamp 2070 for isolating the patient from blood flow in the Cartridge in the event of a fault condition is mounted on the mid-section main control module and coupled to the return tube 2030. The Cartridge Controller subsystem 2001 provides the drive electronics to actuate the return clamp. This pinch clamp is normally closed. The cartridge tubing is normally loaded by the user into these clamps during initial system set-up.

The Oxygenation Cartridge (the Gas-Enrichment Device)

Figure 13:
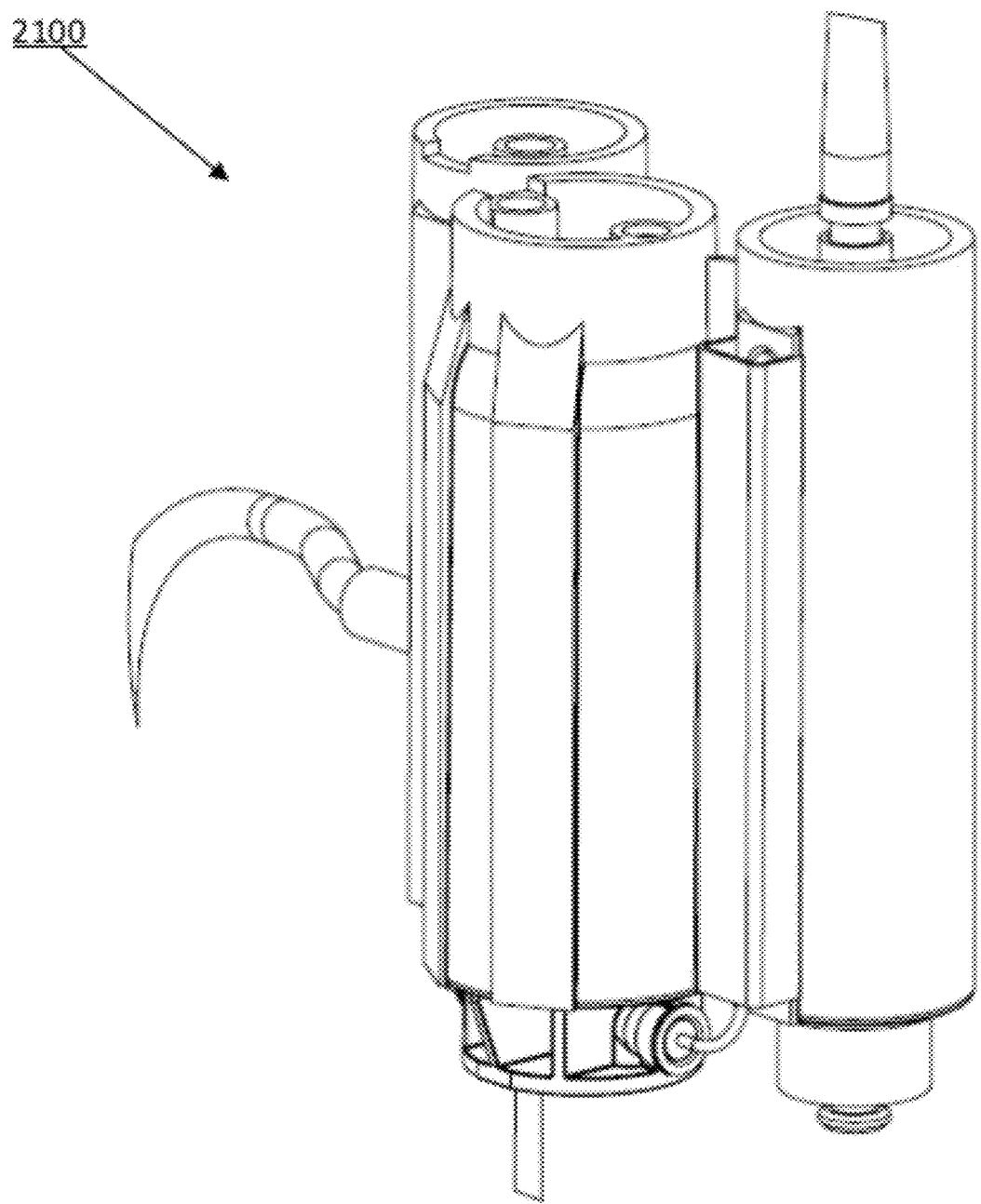
FIG. 13 shows a perspective view of the gas-enrichment device (i.e. the cartridge) in the system of FIG. 2.

In the present preferred embodiment, the Gas-enrichment device is in the form of a Cartridge, as shown FIG. 13. The Cartridge 2100 is a single-use disposable device that is designed to be loaded into the system. The Cartridge has a three-chambered body that creates $SSO_2$ solution from inputs of hospital-supplied oxygen and physiologic saline, and mixes the $SSO_2$ solution with arterial blood within the Cartridge blood path. The Cartridge has a tube set that draws the patient's arterial blood through the draw line, and returns oxygen-supersaturated blood through the return line to the infusion catheter. The Cartridge draw line connects to an arterial sheath. Sheath placement may be coaxial (single arterial access site) or contralateral (two arterial access sites) at the physician's discretion. A physician makes two line connections during the initiation of $SSO_2$ therapy: the Cartridge draw line 2020 is attached to the arterial sheath before priming the blood flow path, and the return line 2030 is attached to the infusion catheter after the blood flow path is successfully primed.

Figure 14:
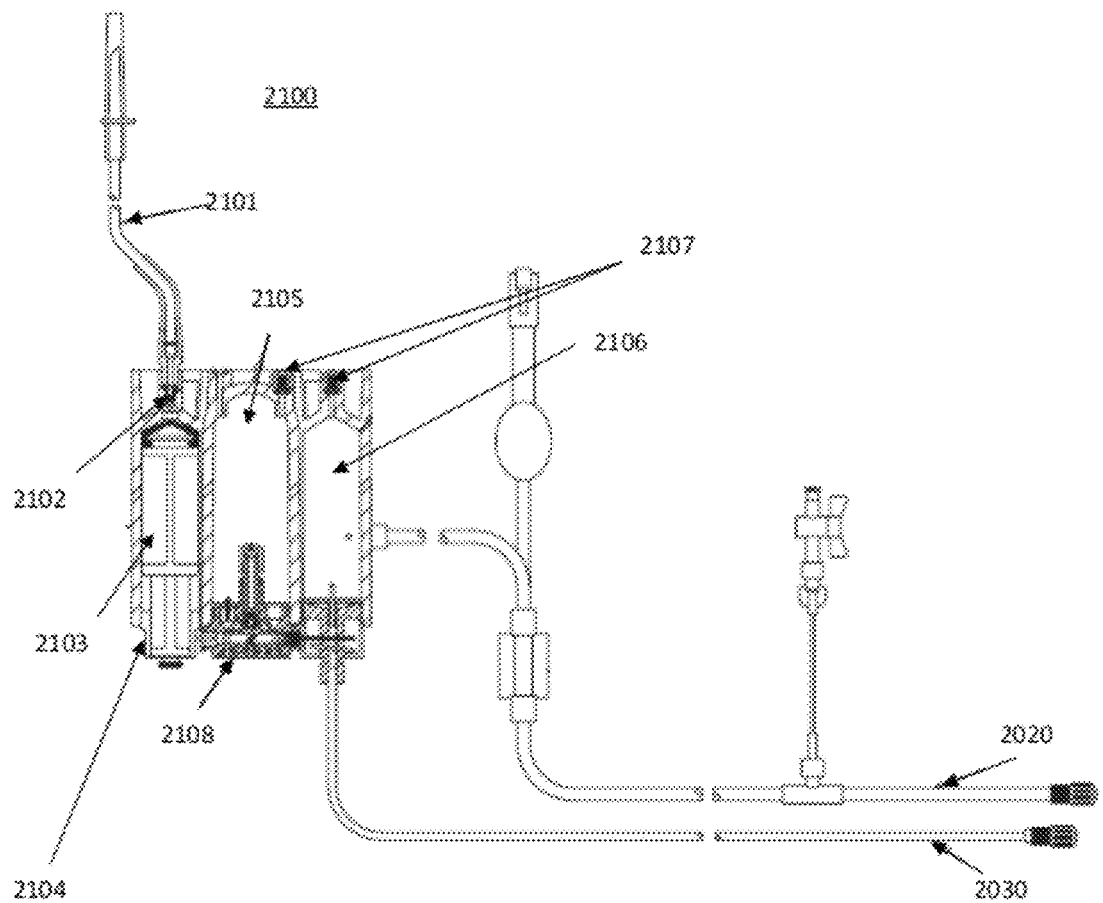
FIG. 14 shows a detailed schematics view of the gas-enrichment device in the system of FIG. 2.

FIG. 14 shows a schematic illustration of the three-chambered structure of the oxygenation Cartridge 2100, which includes the physiologic fluid chamber 2103, the atomization chamber 2105, and the mixing chamber 2106. In operation, saline is drawn from the IV bag into the physiologic fluid chamber 2103, and then pumped into the pressurized atomization chamber 2105. Oxygen is supplied from an oxygen tank and introduced into the atomization chamber 2105, mixing with the atomized saline to form an oxygen-supersaturated physiologic fluid. This oxygen-rich saline is then introduced into the mixing chamber 2106 to be mixed with blood. The blood is drawn into the mixing chamber 2106 through the draw line. Once the blood is mixed with the oxygen-rich saline, the mixture is then returned to the patient through the return line.

As shown in FIGS. 8 and 9, the Cartridge housing 2050 has a door 2051 and grooves for fitting the draw tube 2020 and return tube 2030. The Cartridge Housing 2050 works in conjunction with the Cartridge 2100 during operation. It has a motorized piston actuator that operates the Cartridge piston and delivers saline from an IV bag. The Cartridge Housing 2050 also has a set of needle value actuators to control the flow of liquid through the Cartridge, and vent valve actuators to depressurize the Cartridge oxygen chamber and blood mixing chamber.

FIGS. 8 and 9 show the configuration in which the Cartridge 2100 is loaded in the Cartridge Housing 2050.

FIG. 10 illustrates the location of the pump assembly 2010 in relation to the Cartridge Housing 2050.

Figure 15:
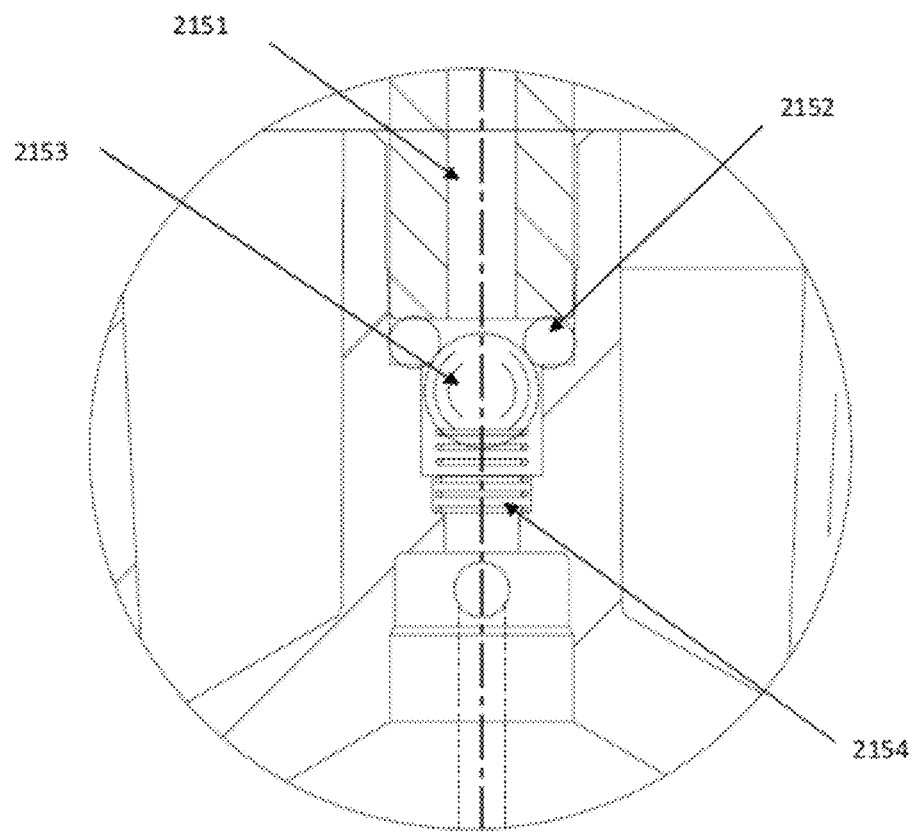
FIG. 15 shows a detailed schematics view of the check valve in the gas-enrichment device of FIG. 14.

Referring to FIGS. 14 and 15, during operation, a tube is coupled to the IV bag to provide saline. The outer end of the tube is coupled to a port on the oxygenation cartridge 2100, forming a passageway that leads to the fluid supply chamber. A check valve 2102 is disposed in the fluid passageway 2151 so that fluid may enter the fluid chamber 2103 through the fluid passageway 2151, but fluid cannot exit through the fluid passageway.

FIG. 15 further illustrates a detailed view of the check valve 2102. Referring to the figure, the check valve 2102 has an O-ring seal 2152 that is disposed between a counter bore in the fluid passageway 2151 and the port. A spring 2154 biases a ball 2153 into contact with the O-ring seal 2152. When fluid moving in the direction of the arrow overcomes the force of the spring and the pressure within the fluid supply chamber, the ball is pushed against the spring so that fluid may flow into the fluid supply chamber. The flow of fluid is unidirectional because the ball efficiently seals against the O-ring seal.

Figure 16:
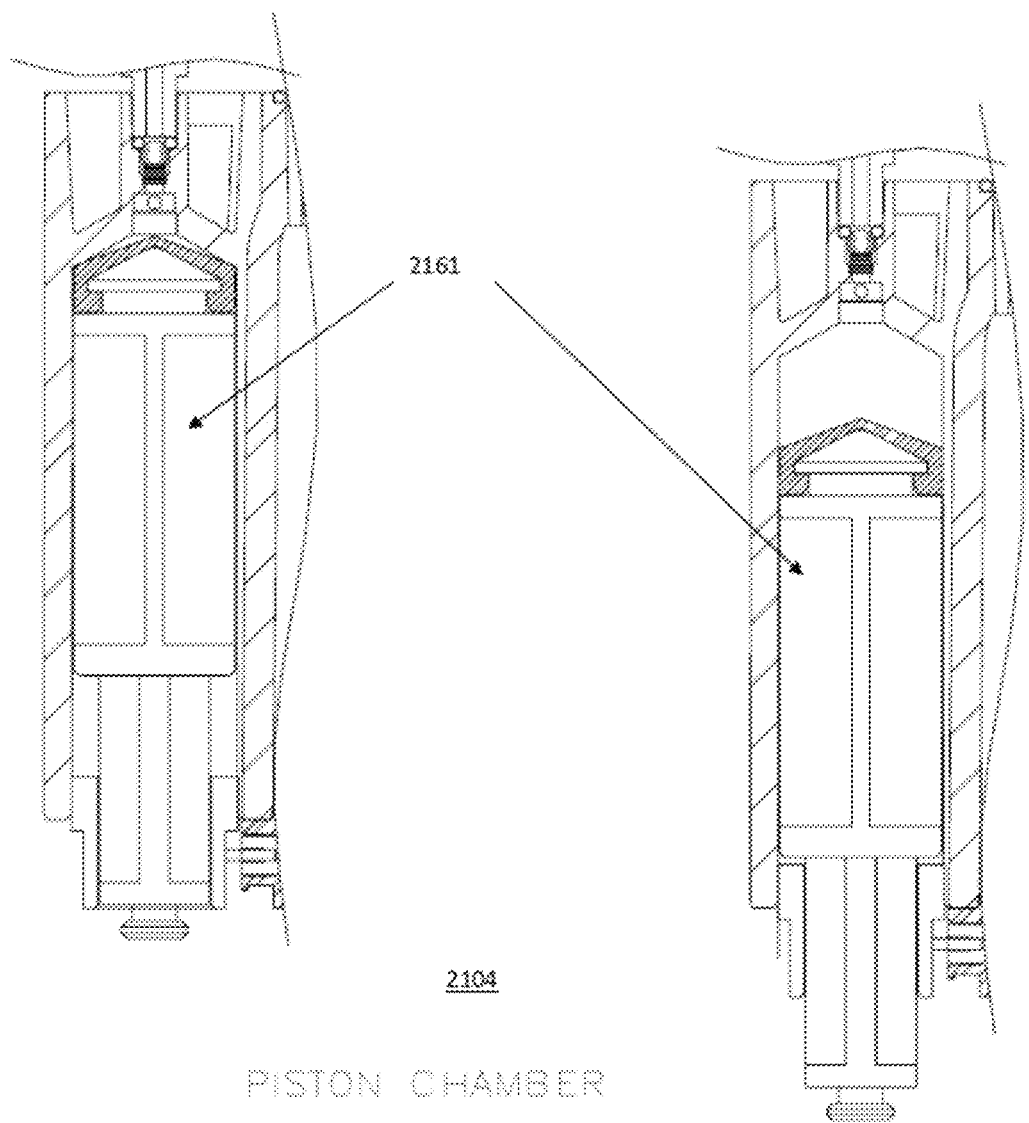
FIG. 16 shows a detailed schematics view of the piston pump in the gas-enrichment device of FIG. 14.

Referring again to FIG. 14, a piston assembly 2104 is located at the opposite end of the fluid supply chamber from the check valve. As illustrated in greater detail in FIG. 16, the piston assembly 2104 is moveable between a first position (left figure) and a second position (right figure). A key is provided at the free end of the piston assembly. The key includes a narrow portion and a relatively wider portion so that it somewhat resembles a doorknob, thus allowing a device to latch onto the ram of the piston actuator assembly and move it between the first and second position.

Referring back again to FIG. 14, the fluid supply chamber 2103 has a second fluid passageway that is coupled to a fluid passageway by a tube. The passageway is an inlet to a valve assembly that controls the manner in which fluid from the fluid supply chamber is delivered into the atomization chamber.

In operation, the piston assembly 2104 within the fluid supply chamber acts as a piston pump. As the piston 2161 retracts, fluid is drawn into the chamber from the fluid supply. No fluid can be drawn from passageway because valve assembly is closed and a check valve is closed in this direction. As the piston 2161 extends, the fluid within the chamber is pressurized, typically to about 650 psig, and expelled from the fluid supply chamber through the fluid passageway. The outlet of the fluid supply chamber is coupled to an inlet of the atomization chamber via an appropriate fluid passageway.

Figure 17:
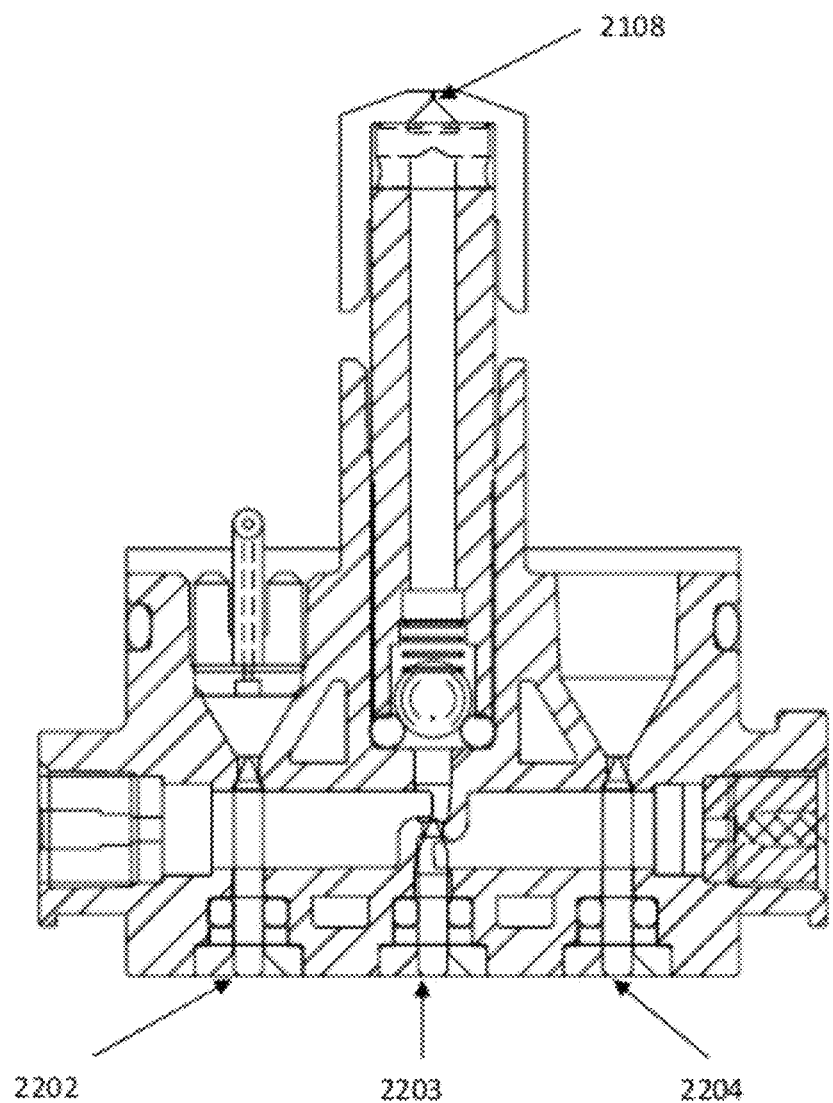
FIG. 17 shows a detailed schematics view of the atomizer assembly in the gas-enrichment device of FIG. 14.

The valve assembly includes three valves: a fill valve 2202, a flush valve 2203, and a flow valve 2204. The system uses needle valves that are normally biased in the closed position as shown in FIG. 17. When the pressure exerted on the needle rises above a certain level, such as about 100 psi and the system actuator is open, the valves will move from the closed position to the opened position, assuming that they are allowed to do so. Push pins and associated actuation mechanisms maintain the valves in the closed positions until one or more of the valves is to be opened.

Oxygen is delivered under pressure to the atomization chamber via a passageway. The oxygen supply is coupled to the inlet of the passageway to provide the desired oxygen supply. If all of the valves are closed, fluid flows from the inlet passageway into a passageway in which the fill valve 2202 is located. Because the cross-sectional area of the passageway is larger than the cross-sectional area of the fill valve 2202, the fluid flows around the closed fill valve and into a passageway that leads to an atomizer.

The atomizer includes a central passageway in which a one-way valve is disposed. The one-way valve is a check valve similar to that described with reference to FIG. 15. Accordingly, when the fluid pressure overcomes the force of the spring in the one-way valve and overcomes the pressure of the oxygen within the atomizer chamber, the fluid travels through the passageway and is expelled from a nozzle 2108 at the end of the atomizer.

The nozzle 2108 forms fluid droplets into which the oxygen within the atomization chamber diffuses as the droplets travel within the atomization chamber. This oxygen-enriched fluid is referred to as supersaturated oxygen ($SSO_2$) solution. The nozzle forms a droplet cone defined by the angle $\alpha$, which is typically about 20 degrees to about 40 degrees at normal operating pressures, e.g., about 550 psig, within the atomization chamber. The nozzle is preferably a simplex-type, swirled pressurized atomizer nozzle including a fluid orifice of about 0.004 inches diameter to 0.005 inches diameter. The droplets infused with the oxygen fall into a pool at the bottom of the atomizer chamber. Since the atomizer will not atomize properly if the level of the pool rises above the level of the nozzle, the level of the pool is controlled to ensure that the atomizer continues to function properly.

By design, oxygen is dissolved within the atomized fluid to a much greater extent than fluid delivered to the atomizer chamber in a non-atomized form. As previously stated, the atomization chamber typically operates at a constant pressure of about 550 psig. Operating the atomizer chamber at 550 psig, or any pressure above 200 psig promotes finer droplet formation of the physiologic solution from the atomizer and better saturation efficiency of the gas in the physiologic fluid than operation at a pressure below 200 psig.

The oxygen-supersaturated fluid formed within the atomizer chamber 2105 is delivered to the mixing chamber 2106 where it is combined with the blood from the patient. Because it is desirable to control the extent to which the patient's blood is enriched with oxygen, and to operate the system at a constant blood flow rate, it may be desirable to dilute the oxygen-supersaturated fluid within the atomizer chamber to reduce its oxygen content. When such dilution is desired, the fill valve is opened to provide a relatively low resistance path for the fluid as compared to the path through the atomizer. Accordingly, instead of passing through the atomizer, the fluid flows through a passageway which extends upwardly into the atomizer chamber via a tube. The tube is advantageously angled somewhat tangentially with respect to the cylindrical wall of the atomizer chamber so that the fluid readily mixes with the oxygen-supersaturated fluid in the pool at the bottom of the atomizer chamber.

Figure 18:
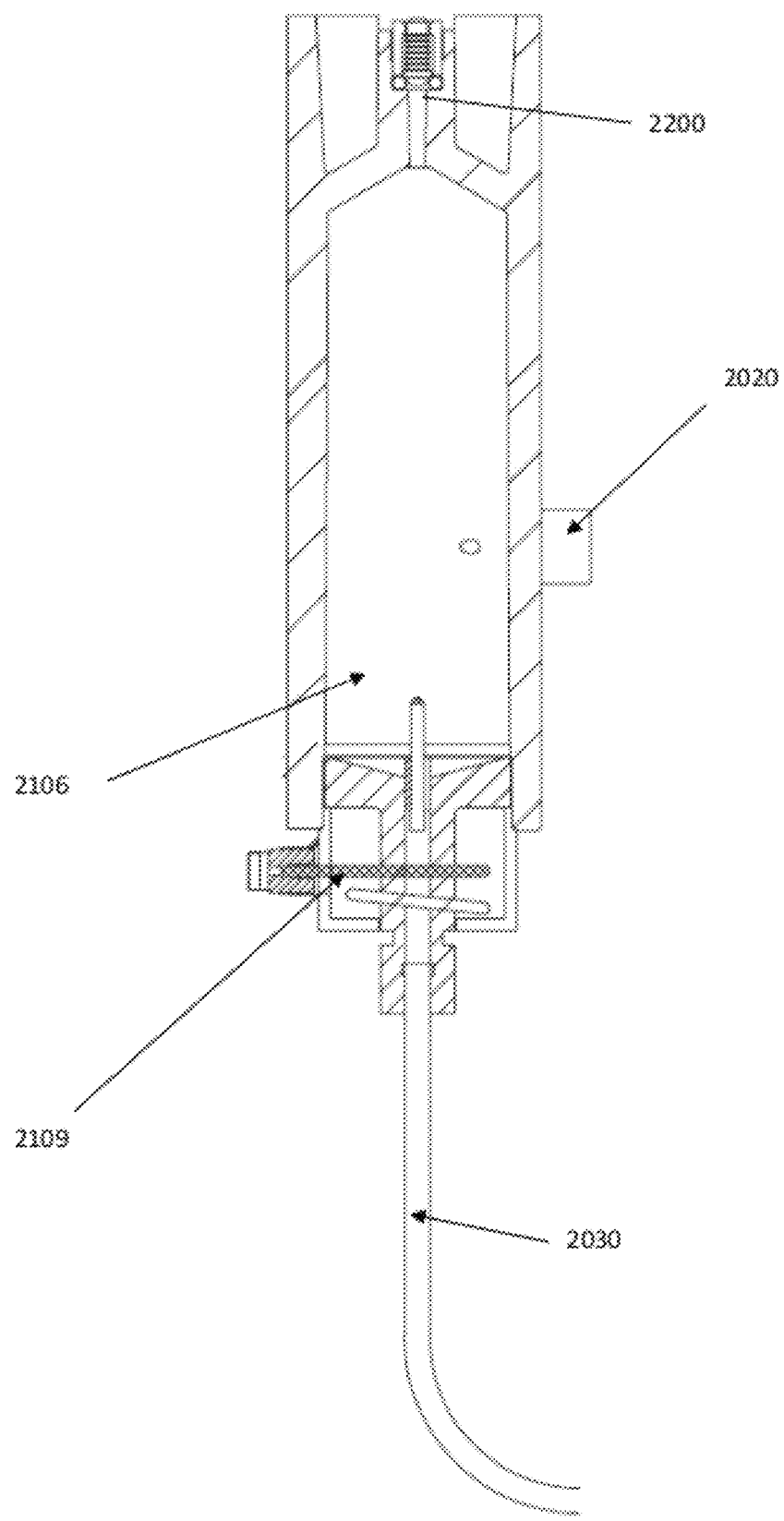
FIG. 18 shows a detailed schematics view of the mixing chamber in the gas-enrichment device of FIG. 14.

The valve assembly essentially performs two additional functions. First, with the fill valve and the flow valve closed, the flush valve may be opened so that fluid flows from the inlet passageway can pass through a series of passageways, the latter of which has a cross-sectional area larger than the cross-sectional area of the flow valve. Thus, the fluid flows out of an outlet passageway that is coupled to a capillary tube 2109 (FIG. 18). The capillary tube terminates in a tip that extends upwardly into the mixing chamber. Since this fluid has not been gas-enriched, it essentially serves to flush the passageways and the capillary tube to remove any contaminants and to ensure adequate fluid flow. Second, with the fill valve and the flush valve closed, the flow valve may be opened when it is desired to deliver the gas-supersaturated fluid from the pool at the bottom of the atomizer chamber into the mixing chamber.

In this second circumstance, the gas-supersaturated fluid readily flows from the atomization chamber through the capillary tube and into the mixing chamber due to the fact that pressure within the atomization chamber is relatively high, e.g., approximately 550 psig, and pressure within the mixing chamber is relatively low, e.g., about 30 psia. The end of the capillary tip is positioned below a blood inlet of the mixing chamber. This spacial arrangement typically ensures that the blood flowing through the draw tube and into the blood inlet effectively mixes with the oxygen-supersaturated fluid flowing into the mixing chamber through the capillary tip. Finally, by the force of the blood pump system, the oxygenated blood is pumped out of the mixing chamber through an outlet into the return tube.

Typically, the capillary tube 2109 and the capillary tip are relatively long to ensure that proper resistance is maintained so that the oxygen within the oxygen-supersaturated fluid remains in solution as it travels from the atomization chamber into the mixing chamber. The capillary tube and the tip are in the range of 50 microns to 300 microns in length and in the range of 3 inches to 20 inches in internal diameter. To maintain the compact size of the oxygenation device, therefore, the capillary tube is wrapped about the exit nozzle of the mixing chamber, as illustrated in the detailed drawing of FIG. 18. To protect the coiled capillary tube from damage, a protective shield is advantageously formed around the coiled capillary tube to create a compartment.

Figure 19:
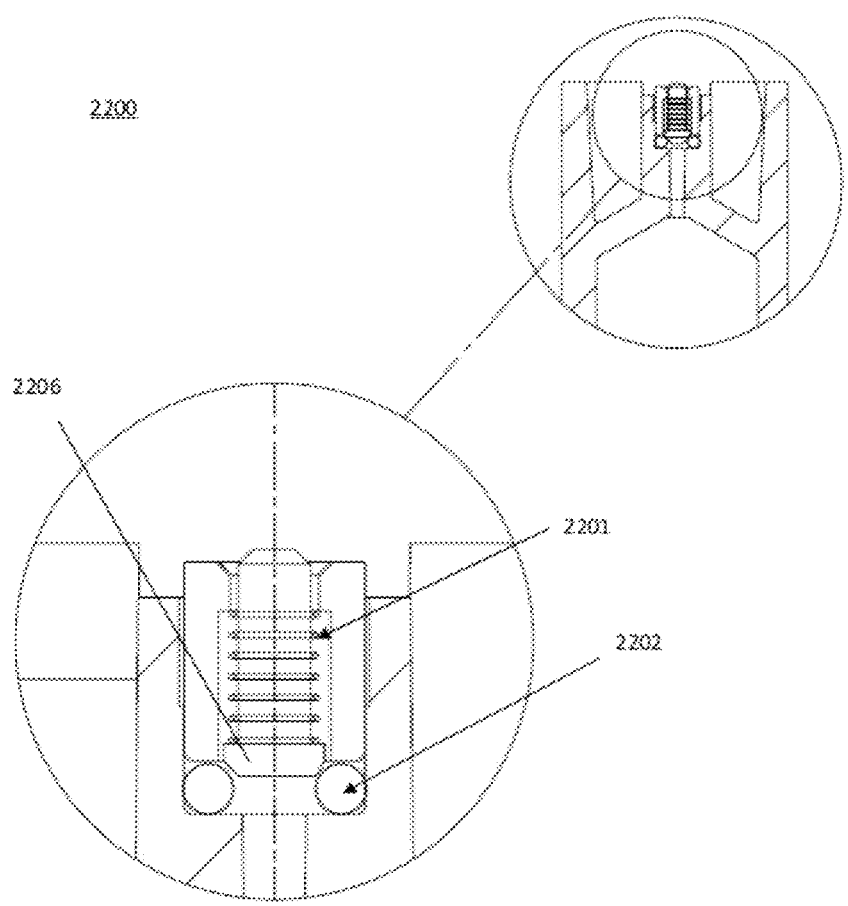
FIG. 19 shows a detailed schematics view of the vent valves in the gas-enrichment device of FIG. 14.

Both the atomization chamber 2105 and the mixing chamber 2106 include vent valves 2200. The vent valves, as illustrated in the detail drawing of FIG. 19, are one-way valves that allow gas pressure to be vented out of the Cartridge and into the atmosphere. The vent valves include a ball or piston head 2206 that is biased in a closed position against an O-ring seal 2202 by a spring 2201. The biasing force is light so that only 1 to 2 psi within the respective chambers is sufficient to move the plunger away from the seal to vent the chamber. Therefore, actuation devices that are part of the cartridge housing and controlled by the system controller normally maintain the valves in the closed position.

As previously mentioned, the Cartridge may optionally include an information recording element for recording data relevant to a procedure, such as flow time, desired concentration, etc. The recording element may be any suitable information recording device such as a bar code label, an RFID chip, a PROM, a flash memory, or any other suitable memory device commonly used in the art. The information recording element may also be used to record relevant patient information such as patient health information (e.g., age, sex, weight, height, etc.), procedural data, and specific system setup information tailored to the receiving patient's treatment plan. Inclusion of such information further enhances operator convenience and patient safety.

When information recording elements are included in the cartridge, the system may further include corresponding means for retrieve and utilizing the information. For example, if a bar code label is used, the system may further include a bar code reader. The on-board cartridge controller may further include an internal database or be connected to an external information system for retrieving information corresponding to the bar code. When the information includes operating parameters such as treatment duration, temperature, concentration, flow rate, etc., they may be automatically utilized by the system controller.

Alternatively, the information retrieving means may be a separate stand-alone system to be used in conjunction with the oxygenation system of the present invention. For example, a stand-along bar code reader may be used to read the bar code on the cartridge by the operator prior to inserting the cartridge into the system.

Cartridge Valve Actuation

The size and shape of the oxygenation Cartridge 2100, the contour of the Cartridge Housing 2050, and the closing of the door 2051 ensure that the Cartridge is positioned in a desired manner within the Cartridge Housing 2050. Correct positioning is important due to the placement of the valves and vents of the Cartridge 2100 and the manner in which they are controlled and actuated. The valves and vents of the Cartridge are actuated using pins. The top of the Cartridge includes two vents, and the bottom of the Cartridge includes three valves. These vents and valves are electromechanically actuated using solenoid-actuated pins.

Figure 20:
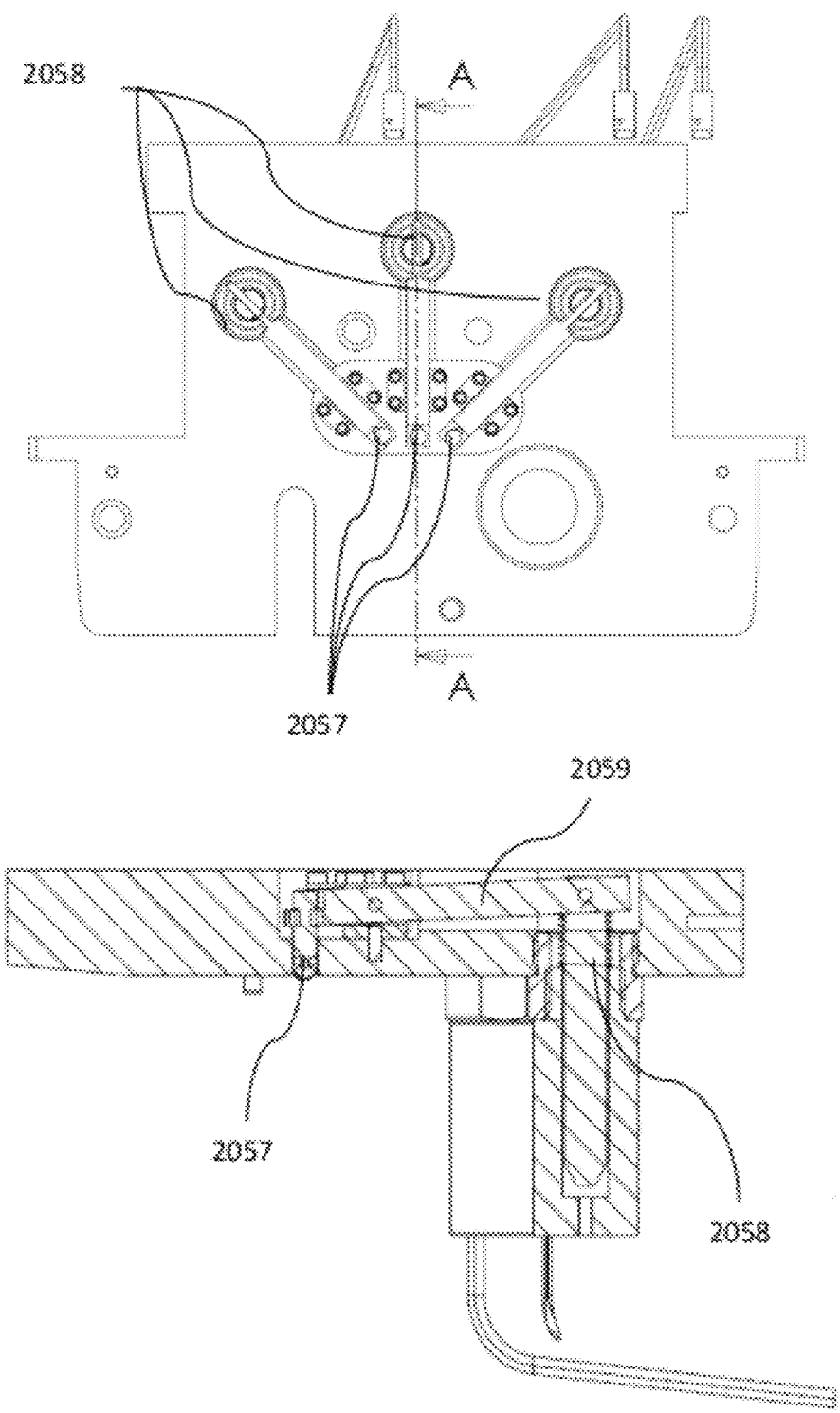
FIG. 20 shows a detailed schematics view from the bottom of the cartridge housing enclosure in the system of FIG. 2.
Figure 21:
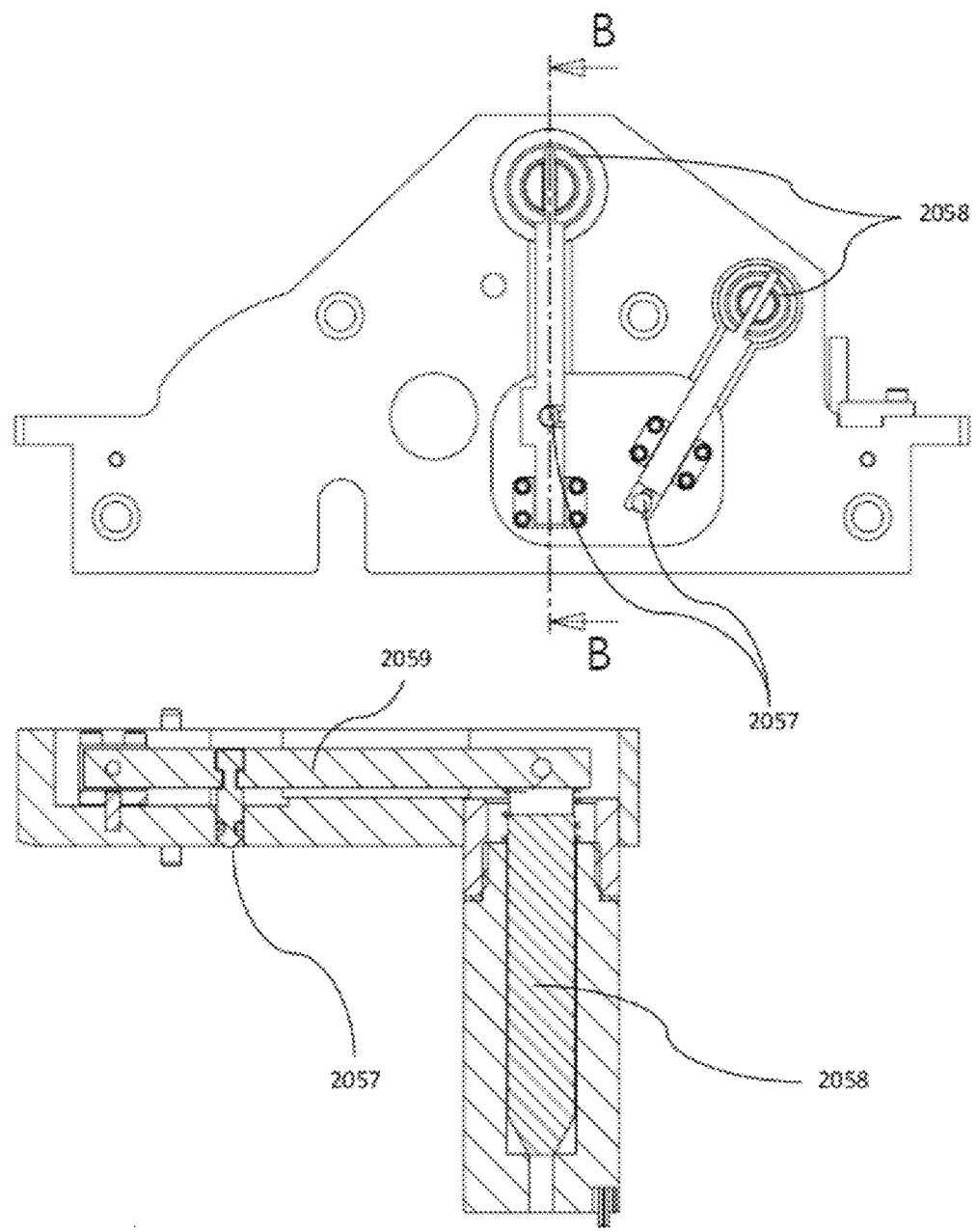
FIG. 21 shows a detailed schematics view from the top of the cartridge housing enclosure in the system of FIG. 2.

A detailed view of these actuation devices is illustrated in FIGS. 20 and 21. Referring first to FIG. 20, a bottom view of the Cartridge Housing is illustrated. It should be noted that the bottom portion of the Cartridge Housing includes a slot through which the blood return tube from the oxygenation Cartridge may pass. Once the oxygenation Cartridge 2100 is in place within the Cartridge Housing 2050, the fill valve 2203, the flush valve 2204, and the flow valve 2205 should be in alignment with respective actuation pins 2057. Each of the pins is tapered at the end to provide an increased tolerance for misalignment. Each of the actuation pins is moved between a closed position and an open position by a respective solenoid 2058. Each of the solenoids is coupled to its respective actuation pin and actuated via a respective lever 2059. Each of the respective levers pivots on a respective fulcrum or pivot pin.

The manner in which the actuators operate may be understood with reference to the cross-sectional views of FIG. 20. The valves are normally held in a closed position. As illustrated in FIG. 20, a piston is urged into an extended position by a spring that biases one end of the lever.

To allow the flush valve 2204 to open, the pin is actuated as illustrated in FIG. 21. The actuation of the solenoid moves the piston generally into a retracted position. The force of the solenoid overcomes the bias of the spring and moves the actuation pin. With the actuation pin in a retracted position, the flush valve 2204 may open.

The oxygen vent valve is normally open and the mixing chamber vent valve is normally closed. Referring now to FIG. 21, a top view of the cartridge housing 2050 is illustrated. The top portion of the cartridge Housing also includes a slot through which the IV tube may pass. Once the cartridge 2100 is properly positioned within the cartridge housing 2050, the vent valves 2200 align with actuation pins, respectively. The pins are also tapered at the ends to increase tolerance to misalignment. Each of the actuation pins is actuated by a respective solenoid. Each of the solenoids is coupled to the respective actuation pins and actuated by a respective lever. Each of the levers pivots about a fulcrum or pivot pin, respectively.

To open the vent valves 2200, the solenoids are actuated. As illustrated in FIG. 21, when the solenoid is actuated, the piston moves into a retracted position. The force of the solenoid overcomes the biasing force of the spring and, thus, the lever moves the actuation pin into a closed position. When the actuation pin is in the retracted position, the vent valve may move upwardly to open and vent gas within the mixing chamber.

The Infusion Catheter

Figure 22:
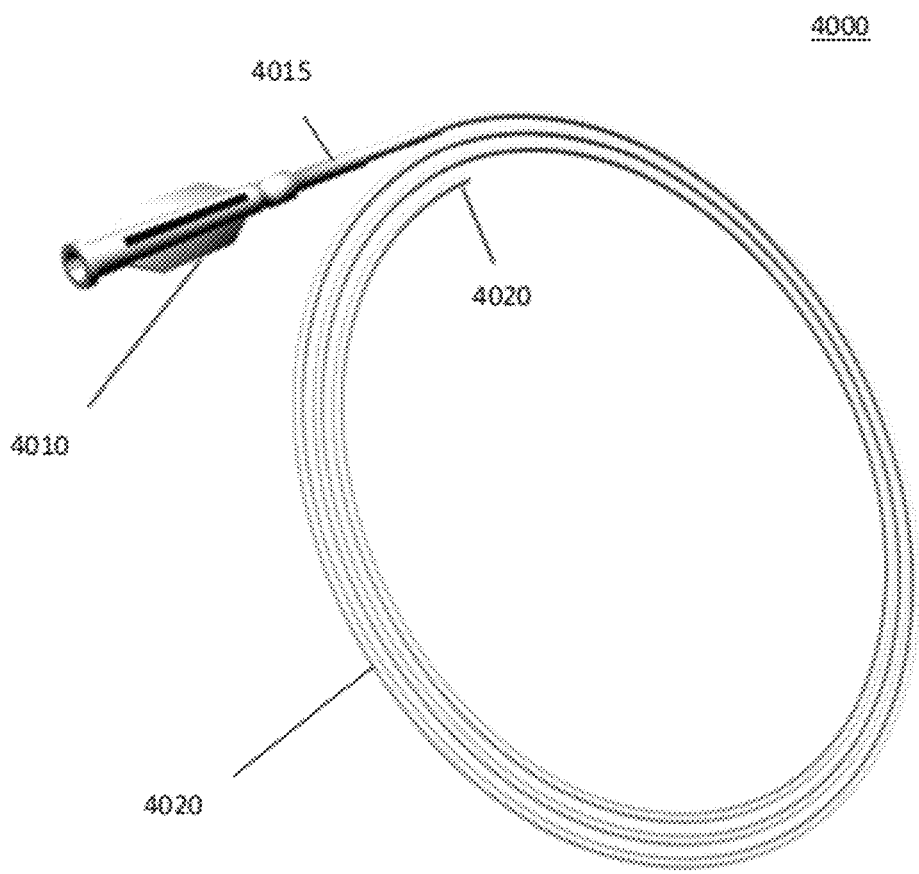
FIG. 22 shows a perspective view of an infusion catheter in accordance with embodiments of the present invention.

FIG. 22 shows an exemplary infusion catheter of the present preferred embodiment. The catheter generally is a sterile, single-use over-the-wire device that may be inserted into patients through commercially available guide catheters 6 F or larger. The catheter's outer diameter (O.D.) is preferably 4.6 French (F) from the distal tip to the proximal strain relief 4015. The catheter is extruded in a continuous process that transitions from soft tip to the stiffer proximal shaft. The nominal usable length is 127 cm and the nominal overall length of the catheter is 135 cm. The inner diameter (I.D.) of the single lumen end-hole catheter is nominally 0.046 in except at the location of the platinum/iridium radiopaque marker band 4020. The I.D. under the marker band is a minimum 0.037 in.

Components of the infusion catheter may include: Luer hub 4010, strain relief 4015, and proximal shaft 4020.

The Luer hub 4010 is a female hub molded over the proximal O.D. of the shaft. The luer hub 4010 enables attachment of the cartridge return tubing to the catheter. A polyolefin strain relief 4015 is applied over the shaft and luer hub 4010 joint with a heat shrinking process.

The infusion catheter preferably has a non-plasticized white high-density polyethylene (HDPE) proximal shaft. The draw tubing connects to the same femoral arterial sheath that may be used for angioplasty and stenting procedures. Sheath placement may be coaxial (in one femoral artery) or contralateral (in both the right and left femoral arteries), at the physician's discretion. FIG. 23 illustrates how arterial blood is withdrawn via the sidearm through the annular space between the guide catheter and sheath; in this configuration (coaxial), a single 8 F introducer sheath can be used. The draw tubing luer fitting connects to the sidearm. The infusion catheter is placed through the 6 F guide catheter over a guidewire, to the desired target location within a coronary artery. The guidewire is removed prior to initiation of blood flow. When extracorporeal blood flow is initiated, the infusion catheter and the return tubing are wet-connected to ensure that no gaseous emboli are introduced to the patient during priming. The term 'wet connection' requires that both devices are fully blood-primed and free of trapped air bubbles. The cartridge return tubing luer fitting connects to the luer hub 4010 of the infusion catheter 4000. For the contralateral approach (not shown), a 5 F introducer sheath is used on the draw side, while a 6 F introducer sheath provides access for the 6 F guide catheter. This alternative approach may be used by physicians who prefer to use two smaller sheaths for arterial access (5 F and 6 F) instead of a single 8 F sheath.

Priming the Fluid Path

As discussed above, the Cartridge of the present preferred embodiment has a three-chambered body. Referring to FIG. 14, the Cartridge 2100, when loaded into the Cartridge Housing enclosure 2050, form a number fluid pathways, notably the extracorporeal circuit pathway, which conducts bodily fluid from the patient through the draw line into the mixing chamber, and then returning the bodily fluid to the patient via the return line, and the physiologic fluid pathway, which draws the physiologic fluid from the physiologic fluid source into the physiologic fluid chamber to be pressurized and transmitted to the atomizing chamber and then directed into the mixing chamber to be mixed with the bodily fluid. Prior to using the system and the Cartridge, the various segments of the fluid paths must be primed with an appropriate fluid.

The physiologic fluid supply chamber 2103 and the atomizing chamber 2105 should be properly primed with the physiologic fluid before beginning of $SSO_2$ administration, whereas the draw line, the mixing chamber, and the return line should be properly primed with the bodily fluid before $SSO_2$ administration. It is an advantageous feature of the present invention that these priming steps are automated by the Cartridge Controller. The generally steps of priming the fluid pathways are outlined as follows:

When the Cartridge is properly loaded into the Cartridge Housing enclosure 2050, and the door 2051 is closed, the system automatically begins the preparatory steps of priming the appropriate Cartridge chambers with the physiologic fluid. During this stage, the system displays a progress message on the display to indicate that preparatory procedures are in progress. During the preparatory procedures, the system also performs a series of diagnostic checks to ensure that the Cartridge and the system are operating normally. Once the system is finished with the initial preparatory procedures, a message is displayed to indicate to the user that priming of the extracorporeal circuit may be initiated.

The user may then connect the extracorporeal circuit by mounting the draw tube in position through the pump head and connected to the patient via a catheter. The return tube is also mounted in position through the combination bubble detector/flow meter 2060 and the return clamp 2070. At this stage, the return clamp 2070 is closed tight to effectively seal off any fluid from exiting the return tube. These steps may be performed either while the system is performing the initial preparatory steps, or after the system indicates that initial preparatory steps are completed.

Once the system has completed the initial preparatory steps and the user has connected the extracorporeal circuit, the user may then begin priming the extracorporeal circuit by pressing the "priming switch" 3040 next to the display. It is an advantageous feature of the present invention that the extracorporeal path priming is automated with built-in safety checks without requiring user intervention. During the first stage of extracorporeal circuit priming, bodily fluid is drawn into the mixing chamber through the draw line while the return clamp 2070 and the vent valve 2107 of the mixing chamber are held closed. As the bodily fluid fills the chamber, hydrostatic pressure will build up in the pathway to verify that all components are properly connected with no leakage in the pathway. The pressure transducer monitors the change in pressure. When a proper pressure is reached (approximately 5 psi), the vent value is opened to allow excess gas to escape. The level sensor in the mixing chamber continues to monitor the level of the bodily fluid in the chamber until the fluid has reached a level appropriate for mixing action to commence. At this point, the return clamp is released and the fluid is allowed to exit the return tube.

After a small amount of bodily fluid has exited the return tube to establish a constant flow rate and pressure, the user verifies that no visible bubble is present in the exiting fluid.

Then, the user makes wet-to-wet connection between the return tube and the infusion catheter to complete the extracorporeal circuit.

In this way, bubble formation is minimized as a result of the fluid pathway design and the priming procedures. No independent or external bubble eliminator is needed in a system of the present invention.

Although the present invention has been described in terms of specific exemplary embodiments and examples, it will be appreciated that the embodiments disclosed herein are for illustrative purposes only and various modifications and alterations might be made by those skilled in the art without departing from the spirit and scope of the invention as set forth in the following claims.

What is claimed is:

1. A gas-enrichment system for enriching a bodily fluid with a gas-enriched fluid, comprising:
    an enclosure configured for receiving a gas-enrichment device;
    an apparatus adapted for connection with a gas tank;
    a controller for processing input information and issuing commands to the components of the system for automatic control of system operations;
    a power supply for providing electrical power to the system; and
    a switching mechanism operatively coupled to the power supply and the gas tank for synchronized switching of the power supply and the gas tank between an ON state and an OFF state,
    wherein said switching mechanism is further coupled to the enclosure so that if the gas-enrichment device is loaded in the enclosure and the switching mechanism is in the ON state, the gas-enrichment device must be unloaded first before the switching mechanism can be switched to the OFF state.

2. The system of claim 1, wherein said switching mechanism comprises a handle slidable along a track between an ON position and an OFF position.

3. The system of claim 2, wherein said handle is connected to the gas tank via a rotatable shaft.

4. The system of claim 3, wherein the gas tank includes a valve that is coupled to the rotatable shaft.

* * * * *